(12) United States Patent
Straub et al.

(10) Patent No.: US 6,833,364 B1
(45) Date of Patent: Dec. 21, 2004

(54) SUBSTITUTED PYRAZOLE DERIVATIVES

(75) Inventors: Alexander Straub, Wuppertal (DE);
Achim Feurer, Odenthal (DE);
Cristina Alonso-Alija, Haan (DE);
Elke Stahl, Bergisch Gladbach (DE);
Johannes-Peter Stasch, Solingen (DE);
Elisabeth Perzborn, Wuppertal (DE);
Joachim Hütter, Wuppertal (DE);
Klaus Dembowsky, Schriesheim (DE)

(73) Assignee: Bayer HealthCare AG, Leverkusen (DE)

( * ) Notice: Subject to any disclaimer, the term of this patent is extended or adjusted under 35 U.S.C. 154(b) by 0 days.

(21) Appl. No.: 09/744,703

(22) PCT Filed: Jul. 16, 1999

(86) PCT No.: PCT/EP99/05073

§ 371 (c)(1),
(2), (4) Date: Mar. 26, 2001

(87) PCT Pub. No.: WO00/06568

PCT Pub. Date: Feb. 10, 2000

(30) Foreign Application Priority Data

Jul. 29, 1998 (DE) .......................................... 198 34 047

(51) Int. Cl.[7] ..................... A61K 31/506; C07D 403/04
(52) U.S. Cl. .................... 514/85; 514/232.2; 514/235.8; 514/236.5; 514/256; 514/269; 544/82; 544/122; 544/123; 544/232; 544/238; 544/243; 544/295; 544/296; 544/319; 544/326; 544/327; 544/328; 544/331; 544/333; 204/157.64
(58) Field of Search ................................ 544/243, 333, 544/296, 295, 82, 122, 123, 319, 328; 514/256, 269, 236.5; 204/157.64

(56) References Cited

U.S. PATENT DOCUMENTS 5,574,168 A    11/1996   Kuo et al. ............... 548/360.5

FOREIGN PATENT DOCUMENTS

| EP | 0667345 | 8/1995 |
| WO | 9816507 | 4/1998 |
| WO | 9823619 | 6/1998 |

OTHER PUBLICATIONS

Corsi, G., Palazzo, G., Germani, C., Scorza, P., and Silvestrini, B., "1–Halobenzyl–1H–Indazole–3–Carboxylic Acids. A New Class of Antispermatogenic Agents", J. Med. Chem. 19(6):778–783 (1976).

*Primary Examiner*—Richard L. Raymond

(57) ABSTRACT

The present invention relates to novel substituted pyrazole derivatives of the general formula (I)

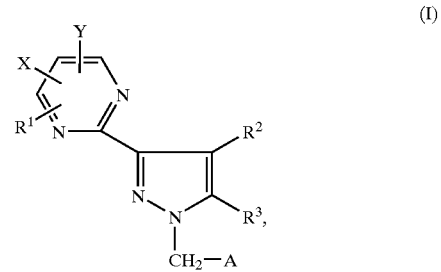

in which the substituents $R^1$, $R^2$, $R^3$, A, X and Y are each as defined, and to processes for their preparation and to their use as medicaments, in particular as medicaments for the treatment of cardiovascular disorders.

13 Claims, 2 Drawing Sheets

Stimulation of soluble guanylate cyclase by 3-(4-amino-5-cyclopropylpyrimidin-2-yl)-1-(2-fluorobenzyl)-1H-pyrazolo[3,4-b]-pyridine (Ex. 1) in the presence of different NO concentrations Effect of 3-(4-amino-5-cyclopropylpyrimidin-2-yl)-1-(2-fluorobenzyl)-1H-pyrazolo[3,4-b]pyridine (Ex. 1) on the average blood pressure of awake, spontanely hypertensive rats

SUBSTITUTED PYRAZOLE DERIVATIVES

This application is a 371 of PCT/EP99/05073, filed Jul. 16, 1999.

The present invention relates to substituted pyrazole derivatives, to processes for their preparation and to their use as medicaments, in particular as medicaments for the treatment of cardiovascular disorders.

It is already known that 1-benzyl-3-(substituted heteroaryl)-fused pyrazole derivatives inhibit thromocyte aggregation (cf. EP 667 345 A1).

WO 98/16223 discloses the use of 1-benzyl-3-(substituted hetaryl)-fused pyrazole derivatives for the treatment of specific disorders of the cardiovascular system and the central nervous system.

WO 98/16507 discloses heterocyclylmethyl-substituted pyrazole derivatives and their use in the treatment of cardiovascular disorders.

WO 98/23619 likewise discloses substituted pyrazole derivatives for the treatment of cardiovascular disorders.

Figure 1:
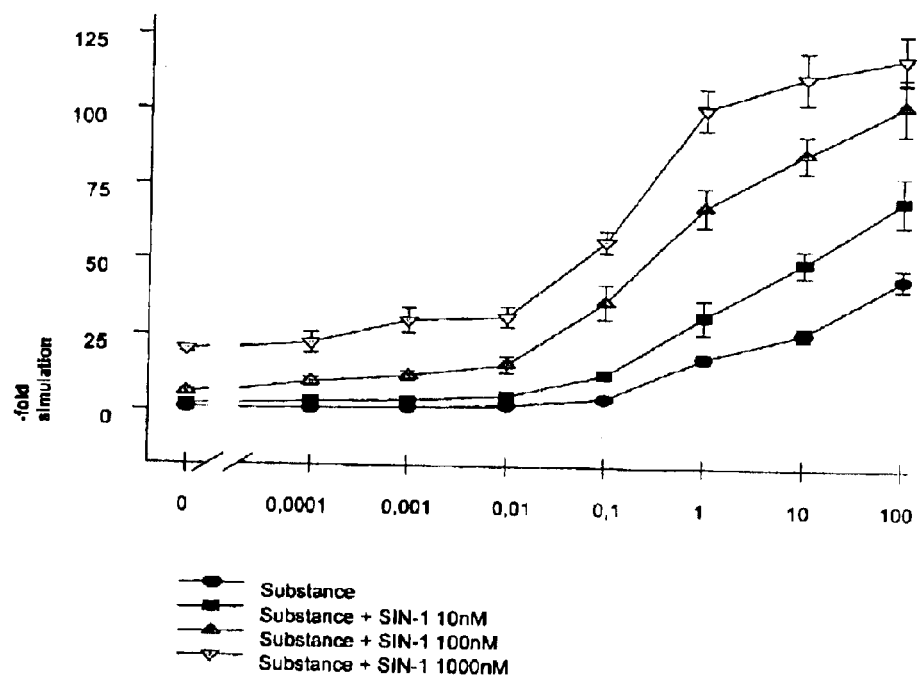
FIG. 1 shows the results of stimulation of soluble guanylate cyclase by 3-(4-amino-5-cyclopropyl-pyrimidin-2-yl)-1 -(2-fluorobenzyl)1H-pyrazolo-[3,4-b]-pyridine (Example 1) in the presence of various NO concentrations.

The present invention relates to substituted pyrazole derivatives of the general formula (I)

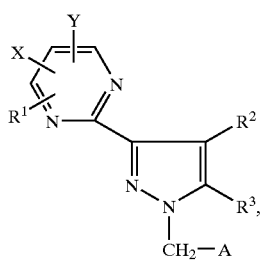

in which
at least one of the substituents $R^1$, X and Y represents saturated or partially unsaturated $C_3$–$C_8$-cycloalkyl, which may optionally be mono- or polysubstituted by amino, azido, formyl, mercaptyl, carboxyl, hydroxyl, morpholino, piperidino, pyrrolidino, sulphonamino, straight-chain, cyclic or branched acyl, acylamino, alkoxy, benzyloxy, alkylamino, dialkylamino, alkylsulphonyl, alkylsulphonamino, alkylthio, alkoxycarbonyl having in each case up to 6 carbon atoms, nitro, cyano, halogen, phenyl and/or is optionally substituted by
straight-chain or branched or cyclic alkyl having up to 6 carbon atoms which for its part may be substituted by amino, mercaptyl, carboxyl, hydroxyl, morpholino, piperidino, pyrrolidino, straight-chain, cyclic or branched acyl, acylamino, alkoxy, alkylamino, dialkylamino, alkylsulphonyl, alkylthio, phenyl, alkylsulphonamino, alkoxycarbonyl having in each case up to 6 carbon atoms, nitro, cyano, halogen, and where the optionally remaining radicals $R^1$, X and/or Y are identical or different and each represents hydrogen, azido, formyl, mercaptyl, carboxyl, hydroxyl, straight-chain or branched acyl, alkoxy, alkylthio or alkoxycarbonyl having in each case up to 6 carbon atoms, nitro, cyano, halogen, phenyl or straight-chain or branched alkenyl or alkinyl having in each case up to 6 carbon atoms or alkyl having up to 20 carbon atoms, where both alkenyl, alkinyl and/or alkyl may optionally be substituted by hydroxyl, amino, azido, carboxyl, straight-chain or branched acyl, alkoxy, alkoxycarbonyl or acylamino having in each case up to 5 carbon atoms, aryl having 6 to 10 carbon atoms, a 5- to 6-membered aromatic heterocycle having up to 3 heteroatoms from the group consisting of S, N and O, halogen, cyano, dialkylamino having up to 6 carbon atoms, alkylamino having up to 6 carbon atoms and/or cycloalkyl having 3 to 8 carbon atoms or by a radical of the formula —$OR^4$,
in which
$R^4$ represents straight-chain or branched acyl having up to 5 carbon atoms,
and/or the optionally remaining radicals $R^1$, X and/or Y each represent a radical of the formula

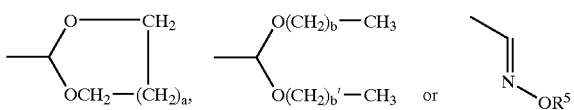

in which
a, b and b' are identical or different and represent a number 0, 1, 2 or 3,
$R^5$ represents hydrogen or straight-chain or branched alkyl having up to 4 carbon atoms,
and/or the optionally remaining radicals $R^1$, X and/or Y each represent a 3- to 8-membered ring, which may also be linked to the pyrimidine via a —CO-bridge, and which may be saturated, unsaturated and/or partially unsaturated, which may contain 1 to 4 heteroatoms from the group consisting of N, O, S, SO, $SO_2$, which may also be attached via N, which may optionally contain a carbonyl group as ring member and which is optionally mono- or polysubstituted by identical or different substituents from the group consisting of straight-chain or branched alkyl having up to 6 carbon atoms which is optionally substituted by hydroxyl, amino, halogen, carboxyl, straight-chain or branched acyl, alkoxy, alkoxycarbonyl or acylamino having in each case up to 5 carbon atoms,
and/or the optionally remaining radicals $R^1$, X and/or Y each represent straight-chain or branched acyl having up to 6 carbon atoms which is optionally substituted by halogen, or
represent straight-chain or branched acyloxy having up to 6 carbon atoms, or
represent arylthio having 6 to 10 carbon atoms or heteroarylthio,
and/or the optionally remaining radicals $R^1$, X and/or Y represent radicals of the formulae —$SO_3H$ or $S(O)_cR^6$,
in which
c represents a number 1 or 2,
$R^6$ represents straight-chain or branched alkyl having 1 to 10 carbon atoms, cycloalkyl having 3 to 8 carbon atoms, aryl having 6 to 10 carbon atoms or a 5- to 6-membered heterocycle having up to 3 heteroatoms from the group consisting of S, N and O, where the ring systems may optionally be substituted by halogen or by straight-chain or branched alkyl or alkoxy having in each case up to 4 carbon atoms, and/or the optionally remaining radicals $R^1$, X and/or Y each represent a radical of the formula $PO(OR^7)(OR^8)$, in which $R^7$ and $R^8$ are identical or different and each represents hydrogen, straight-chain or branched alkyl having up to 8 carbon atoms or cycloalkyl having 3 to 8 carbon atoms, aryl having 6 to 10 carbon atoms or benzyl, and/or the optionally remaining radicals $R^1$, X and/or Y each represents oxycycloalkyl having 3 to 8 carbon atoms or represent radicals of the formulae —NH—C(=NH)NH$_2$, CON=C(NH$_2$)$_2$ or —C=NH(NH$_2$), (CO)$_d$NR$^9$R$^{10}$ or —NHCONR$^{9'}$R$^{10'}$, in which d represents a number 0 or 1, $R^9$ and $R^{10}$ are identical or different and each represents hydrogen, straight-chain or branched alkyl having up to 14 carbon atoms or cycloalkyl having 3 to 14 carbon atoms, aryl having 6 to 10 carbon atoms or a 3- to 10-membered ring having up to 5 heteroatoms from the group consisting of N, O, S, which may also be attached via N, where the abovementioned radicals may optionally be substituted by aryl having 6 to 10 carbon atoms, heterocyclyl, cycloalkyl having 3 to 7 carbon atoms, hydroxyl, amino or straight-chain or branched alkoxy, acyl or alkoxycarbonyl having in each case up to 6 carbon atoms, and in the case that d=0, $R^9$ and $R^{10}$ may also represent straight-chain, branched or cyclic acyl having up to 14 carbon atoms, straight-chain or branched hydroxyalkyl having up to 6 carbon atoms, straight-chain or branched alkoxyalkyl having a total of up to 12 carbon atoms, straight-chain or branched alkoxycarbonyl or acyloxyalkyl having in each case up to 6 carbon atoms or a radical of the formula —SO$_2$R$^{11}$ or radicals of the formulae

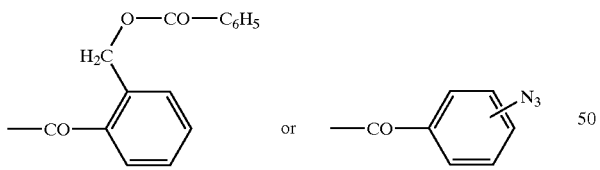

in which $R^{11}$ represents straight-chain or branched alkyl having up to 4 carbon atoms, and/or $R^9$ and $R^{10}$ represent radicals of the formulae

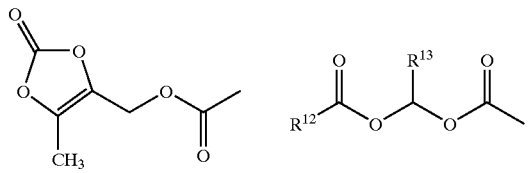

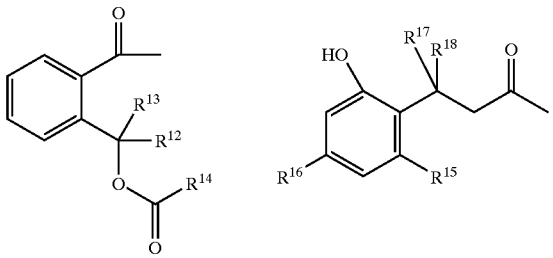

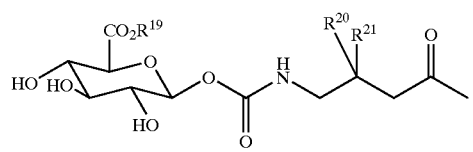

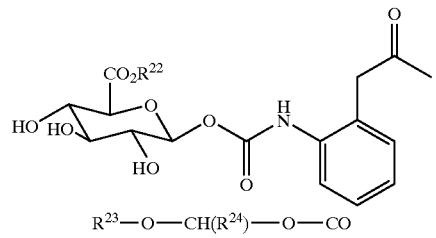

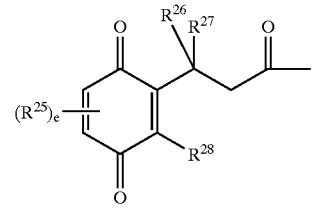

in which $R^{12}$, $R^{13}$ and $R^{15}$ to $R^{28}$ are identical or different and each represents hydrogen or straight-chain or branched alkyl having up to 4 carbon atoms, e represents a number 0, 1 or 2, and $R^{14}$ represents straight-chain or branched alkyl having up to 6 carbon atoms or cycloalkyl having 3 to 8 carbon atoms, $R^{9'}$ and $R^{10'}$ are identical or different and each represents hydrogen; alkyl having up to 14 carbon atoms which is optionally substituted by hydroxyl or alkoxy having up to 8 carbon atoms; aryl having 6 to 10 carbon atoms which is optionally substituted by halogen, $R^2$ and $R^3$ form, together with the double bond, a fused phenyl ring or a fused 6-membered saturated or aromatic heterocycle having up to 3 heteroatoms from the group consisting of N, S and O, which is optionally substituted up to 3 times by identical or different substituents from the group consisting of formyl, carboxyl, hydroxyl, mercaptyl, straight-chain or branched acyl, alkylthio or alkoxycarbonyl having in each case up to 6 carbon atoms, nitro, cyano, halogen or straight-chain or branched alkyl or alkoxy having in each case up to 6 carbon atoms which for its part may be substituted by hydroxyl, amino, carboxyl, straight-chain or branched acyl, alkoxy or alkoxycarbonyl having in each case up to 5 carbon atoms, and/or the fused phenyl ring or the fused 6-membered saturated or aromatic heterocycle is optionally substituted by a group of the formula —NR$^{29}$R$^{30}$, in which
- $R^{29}$ and $R^{30}$ are identical or different and each represents hydrogen or straight-chain or branched alkyl having up to 6 carbon atoms, or
- $R^{29}$ represents hydrogen and
- $R^{30}$ represents acyl having up to four carbon atoms and/or the fused phenyl ring or the fused 6-membered saturated or aromatic heterocycle are optionally substituted by phenyl which for its part may be substituted up to 2 times by identical or different substituents from the group consisting of halogen, straight-chain or branched alkyl and alkoxy having in each case up to 6 carbon atoms and/or the fused phenyl ring or the fused 6-membered saturated or aromatic heterocycle are optionally substituted by a group of the formula —N═CH—NR$^{31}$R$^{32}$, in which
- $R^{31}$ and $R^{32}$ are identical or different and each represents hydrogen, phenyl or straight-chain or branched alkyl having up to 6 carbon atoms, A represents a 5- or 6-membered aromatic or saturated heterocycle having up to 3 heteroatoms from the group consisting of S, N and O or represents phenyl, which are optionally substituted up to 3 times by identical or different substituents from the group consisting of amino, mercaptyl, hydroxyl, formyl, carboxyl, straight-chain or branched acyl, alkylthio, alkyloxyacyl, alkoxy or alkoxycarbonyl having in each case up to 6 carbon atoms, nitro, cyano, trifluoromethyl, azido, halogen, phenyl and straight-chain or branched alkyl having up to 6 carbon atoms which for its part may be substituted by hydroxyl, carboxyl, straight-chain or branched acyl, alkoxy or alkoxycarbonyl having in each case up to 5 carbon atoms, and/or is substituted by a group of the formula —(CO)$_f$—NR$^{33}$R$^{34}$, in which
- f represents a number 0 or 1,
- $R^{33}$ and $R^{34}$ are identical or different and each represents hydrogen, phenyl, benzyl or straight-chain or branched alkyl or acyl having in each case up to 5 carbon atoms, and their isomeric forms and salts.

The compounds of the general formula (I) according to the invention may also be present in the form of their salts. In general, salts with organic or inorganic bases or acids may be mentioned here.

In the context of the present invention, preference is given to physiologically acceptable salts. Physiologically acceptable salts of the compounds according to the invention may be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, p-toluenesulphonic acid, benzenesulphonic acid, naphthalenedispulphonic acid, acetic acid, propionic acid, lactic acid, tartaric acid, citric acid, fumaric acid, maleic acid or benzoic acid.

Physiologically acceptable salts may also be the metal or ammonium salts of the compounds according to the invention which have a free carboxyl group. Particular preference is given, for example, to sodium, potassium, magnesium or calcium salts, and to ammonium salts which are derived from ammonia, or organic amines, such as, for example, ethylamine, di- or triethylamine, di- or triethanolamine, dicyclohexyl-amine, dimethylaminoethanol, arginine, lysine or ethylenediamine.

The compounds according to the invention may exist in stereoisomeric forms which are either like image and mirror image (enantiomers) or which are not like image and mirror image (diastereomers). The invention relates both to the enantiomers or diastereomers and to their respective mixtures. The racemates, like the diastereomers, can be separated into stereoisomerically uniform components in a known manner.

In the context of the present invention, the substituents have, unless indicated otherwise, generally the following meanings:

Alkyl generally represents a straight-chain or branched hydrocarbon radical having 1 to 20 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl, nonyl, decyl, dodecyl, eicosyl.

Alkenyl generally represents a straight-chain or branched hydrocarbon radical having 2 to 20 carbon atoms and one or more, preferably one or two, double bonds. Examples which may be mentioned are allyl, propenyl, isopropenyl, butenyl, isobutenyl, pentenyl, isopentenyl, hexenyl, isohexenyl, heptenyl, isoheptenyl, octenyl, isooctenyl.

Alkinyl generally represents a straight-chain or branched hydrocarbon radical having 2 to 20 carbon atoms and one or more, preferably one or two, triple bonds. Examples which may be mentioned are ethinyl, 2-butinyl, 2-pentinyl and 2-hexinyl.

Acyl generally represents straight-chain or branched lower alkyl having 1 to 9 carbon atoms which is attached via a carbonyl group. Examples which may be mentioned are: acetyl, ethylcarbonyl, propylcarbonyl, isopropylcarbonyl, butylcarbonyl and isobutylcarbonyl.

Alkoxy generally represents a straight-chain or branched hydrocarbon radical having 1 to 14 carbon atoms which is attached via an oxygen atom. Examples which may be mentioned are methoxy, ethoxy, propoxy, isopropoxy, butoxy, isobutoxy, pentoxy isopentoxy, hexoxy, isohexoxy, heptoxy, isoheptoxy, octoxy or isooctoxy. The terms "alkoxy" and "alkyloxy" are used synonymously.

Alkoxyalkyl generally represents an alkyl radical having up to 8 carbon atoms which is substituted by an alkoxy radical having up to 8 carbon atoms.

Alkoxycarbonyl can be depicted, for example, by the formula

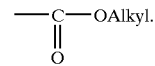

Alkyl here generally represents a straight-chain or branched hydrocarbon radical having 1 to 13 carbon atoms. The following alkoxycarbonyl radicals may be mentioned as examples: methoxycarbonyl, ethoxycarbonyl, propoxycarbonyl, isopropoxycarbonyl, butoxycarbonyl or isobutoxycarbonyl.

Cycloalkyl generally represents a cyclic hydrocarbon radical having 3 to 8 carbon atoms. Preference is given to cyclopropyl, cyclopentyl and cyclohexyl. Examples which may be mentioned are cyclopentyl, cyclohexyl, cycloheptyl and cyclooctyl.

Cycloalkoxy represents, in the context of the invention, an alkoxy radical whose hydrocarbon radical is a cycloalkyl radical. The cycloalkyl radical generally has up to 8 carbon atoms. Examples which may be mentioned are: cyclopropyloxy and cyclohexyloxy. The terms "cycloalkoxy" and "cycloalkyloxy" are used synonymously.

Aryl generally represents an aromatic radical having 6 to 10 carbon atoms. Preferred aryl radicals are phenyl and naphthyl.

Halogen represents, in the context of the invention, fluorine, chlorine, bromine and iodine.

Heterocycle represents, in the context of the invention, a saturated, unsaturated or aromatic 3- to 10-membered, for example 5- or 6-membered, heterocycle which may contain up to 3 heteroatoms from the group consisting of S, N and O and which, in the case of a nitrogen atom, may also be attached via this nitrogen atom. Examples which may be mentioned are: oxadiazolyl, thiadiazolyl, pyrazolyl, pyridyl, pyrimidinyl, pyridazinyl, pyrazinyl, thienyl, furyl, pyrrolyl, pyrrolidinyl, piperazinyl, tetrahydropyranyl, tetrahydrofuranyl, 1,2,3-triazolyl, thiazolyl, oxazolyl, imidazolyl, morpholinyl or piperidyl. Preference is given to thiazolyl, furyl, oxazolyl, pyrazolyl, triazolyl, pyridyl, pyrimidinyl, pyridazinyl and tetrahydropyranyl. The term "heteroaryl" (or "hetaryl") represents an aromatic heterocyclic radical.

Preference is given to compounds of the general formula (I) according to the invention,
in which at least one of the substituents $R^1$, X and Y represents cyclopropyl, cyclobutyl, cyclopentenyl, cyclopentyl, cyclohexyl or cycloheptyl which may optionally be mono- or polysubstituted by amino, azido, formyl, mercaptyl, carboxyl, hydroxyl, morpholino, piperidino, pyrrolidino, sulphonamino, straight-chain, cyclic or branched acyl, acylamino, alkoxy, benzyloxy, alkylamino, dialkylamino, alkylsulphonyl, alkylsulphonamino, alkylthio, alkoxycarbonyl having in each case up to 4 carbon atoms, nitro, cyano, halogen, phenyl and/or is optionally substituted by straight-chain or branched or cyclic alkyl having up to 4 carbon atoms which for its part may be substituted by amino, mercaptyl, carboxyl, hydroxyl, morpholino, piperidino, pyrrolidino, straight-chain, cyclic or branched acyl, acylamino, alkoxy, alkylamino, dialkylamino, alkylsulphonyl, alkylthio, phenyl, alkylsulphonamino, alkoxycarbonyl having in each case up to 4 carbon atoms, nitro, cyano, halogen, and where the optionally remaining radicals $R^1$, X and/or Y are identical or different and each represents hydrogen, azido, formyl, mercaptyl, carboxyl, hydroxyl, straight-chain or branched acyl, alkoxy, alkylthio or alkoxycarbonyl having in each case up to 4 carbon atoms, nitro, cyano, halogen, phenyl or straight-chain or branched alkenyl or alkinyl having in each case up to 4 carbon atoms or alkyl having up to 18 carbon atoms, where both alkenyl, alkinyl and/or alkyl may optionally be substituted by hydroxyl, amino, azido, carboxyl, straight-chain or branched acyl, alkoxy, alkoxycarbonyl or acylamino having in each case up to 4 carbon atoms, phenyl, naphthyl or pyridyl, halogen, cyano, dialkylamino having up to 6 carbon atoms, alkylamino having up to 4 carbon atoms and/or cyclopropyl, cyclopentyl, cyclohexyl or by a radical of the formula —$OR^4$, in which
$R^4$ represents straight-chain or branched acyl having up to 4 carbon atoms, and/or the optionally remaining radicals $R^1$, X and/or Y each represent a radical of the formula

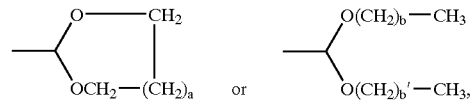

in which
a, b and b' are identical or different and represent a number 0, 1 or 2, and/or the optionally remaining radicals $R^1$, X and/or Y each represent a 3- to 8-membered ring, which may also be linked to the pyrimidine via a —CO-bridge, and which may be saturated, unsaturated and/or partially unsaturated, which may contain 1 to 3 heteroatoms from the group consisting of N, O, S, SO, $SO_2$, which may also be attached via N, which may optionally contain a carbonyl group as ring member and which is optionally mono- or polysubstituted by identical or different substituents from the group consisting of straight-chain or branched alkyl having up to 4 carbon atoms which is optionally substituted by hydroxyl, amino, halogen, carboxyl, straight-chain or branched acyl, alkoxy, alkoxycarbonyl or acylamino having in each case up to 4 carbon atoms, and/or the optionally remaining radicals $R^1$, X and/or Y each represent straight-chain or branched acyl having up to 4 carbon atoms which is optionally substituted by halogen, or represent straight-chain or branched acyloxy having up to 4 carbon atoms, or represent phenylthio, and/or represent radicals of the formulae —$SO_3H$ or $S(O)_cR^6$, in which c represents a number 1 or 2, $R^6$ represents straight-chain or branched alkyl having 1 to 8 carbon atoms, phenyl or a 5- to 6-membered heterocycle having up to 2 heteroatoms from the group consisting of S, N and/or O, where the ring systems may optionally be substituted by halogen or by straight-chain or branched alkyl or alkoxy having in each case up to 3 carbon atoms, and/or the optionally remaining radicals $R^1$, X and/or Y each represent a radical of the formula $PO(OR^7)(OR^8)$,
in which $R^7$ and $R^8$ are identical or different and each represents hydrogen, straight-chain or branched alkyl having up to 4 carbon atoms or cyclopropyl, cyclopentyl, phenyl or benzyl, and/or the optionally remaining radicals $R^1$, X and/or Y each represent oxycycloalkyl having 3 to 6 carbon atoms or represent radicals of the formulae —NH—C(=NH)$NH_2$, —CON=C($NH_2$)$_2$ or —C=NH($NH_2$), $(CO)_dNR^9R^{10}$ or —NHCONR$^{9'}R^{10'}$,
in which d represents a number 0 or 1, $R^9$ and $R^{10}$ are identical or different and each represents hydrogen, straight-chain or branched alkyl having up to 4 carbon atoms or cyclopropyl, cyclopentyl, cyclohexyl, phenyl or a 3- to 6-membered ring having up to 3 heteroatoms from the group consisting of N, O, S, which may also be attached via N, where the abovementioned radicals may optionally be substituted phenyl, cyclopropyl, cyclopentyl, hydroxyl, amino or straight-chain or branched alkoxy, acyl or alkoxycarbonyl having in each case tip to 4 carbon atoms, and in the case that d=0, $R^9$ and $R^{10}$ may also represent straight-chain, branched or cyclic acyl having up to 6 carbon atoms, straight-chain or branched hydroxyalkyl having up to 4 carbon atoms, straight-chain or branched alkoxyalkyl having a total of up to 10 carbon atoms, straight-chain or branched alkoxycarbonyl or acyloxyalkyl having in each case up to 4 carbon atoms or a radical of the formula —$SO_2R^{11}$ or a radical of the formulae

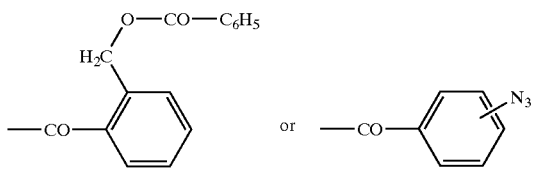

in which $R^{11}$ represents straight-chain or branched alkyl having up to 3 carbon atoms, and/or $R^9$ and $R^{10}$ represent radicals of the formulae

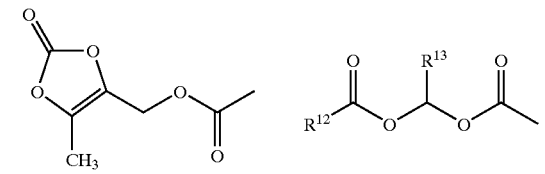

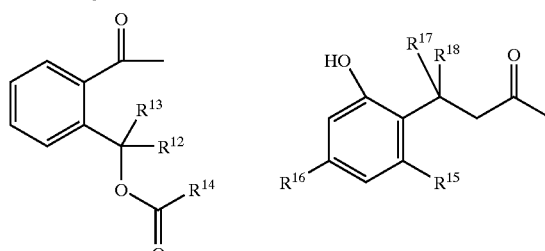

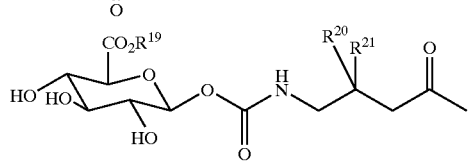

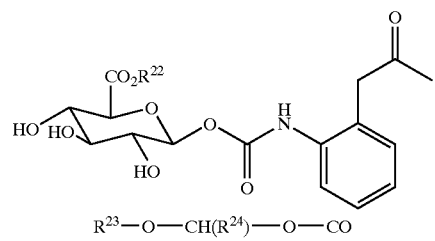

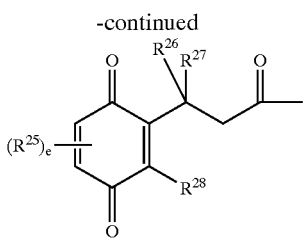

in which $R^{12}$, $R^{13}$ and $R^{15}$ to $R^{28}$ are identical or different and each represents hydrogen or straight-chain or branched alkyl having up to 4 carbon atoms, e represents a number 0, 1 or 2, and $R^{14}$ represents straight-chain or branched alkyl having up to 6 carbon atoms or cycloalkyl having 3 to 8 carbon atoms, $R^{9'}$ and $R^{10'}$ are identical or different and each represents hydrogen; alkyl having up to 4 carbon atoms which is optionally substituted by hydroxyl or alkoxy having up to 7 carbon atoms, phenyl which is optionally substituted by halogen, $R^2$ and $R^3$, together with the double bond, form a fused phenyl, pyridyl, pyrimidinyl, pyrazinyl or pyridazinyl ring, which are optionally substituted up to 2 times by identical or different substituents from the group consisting of formyl, carboxyl, hydroxyl, mercaptyl, straight-chain or branched acyl, alkylthio or alkoxycarbonyl having in each case up to 5 carbon atoms, nitro, cyano, azido, fluorine, chlorine, bromine or straight-chain or branched alkyl or alkoxy having in each case up to 5 carbon atoms which for its part may be substituted by hydroxyl, amino, carboxyl, straight-chain or branched acyl, alkoxy or alkoxycarbonyl having in each case up to 4 carbon atoms, and/or the abovementioned heterocyclic rings or phenyl are optionally substituted by a group of the formula —$NR^{29}R^{30}$, in which $R^{29}$ and $R^{30}$ are identical or different each and represents hydrogen or straight-chain or branched alkyl having up to 4 carbon atoms or $R^{29}$ represents hydrogen and $R^{30}$ represents formyl and/or the abovementioned fused phenyl, pyridyl, pyrimidinyl, pyrazinyl or pyridazinyl rings are optionally substituted by phenyl which for its part may be substituted by fluorine, chlorine, bromine or by straight-chain or branched alkyl or alkoxy having in each case up to 4 carbon atoms, A represents thienyl, tetrahydropyranyl, tetrahydrofuranyl, phenyl, morpholinyl, pyrimidyl, pyrazinyl, pyridazinyl or pyridyl which are optionally substituted up to 2 times by identical or different substituents from the group consisting of hydroxyl, formyl, carboxyl, straight-chain or branched acyl, alkylthio, alkyloxyacyl, alkoxy or alkoxycarbonyl having in each case up to 4 carbon atoms, fluorine, chlorine or bromine, and their isomeric forms and salts.

Particular preference is given to compounds of the general formula (I) according to the invention, in which at least one of the substituents $R^1$, X and Y represents cyclopropyl which is optionally substituted by hydroxyl or fluoromethyl, or represents cyclobutyl, cyclopentenyl, cyclopentyl or cyclohexyl, and where the optionally remaining radicals $R^1$, X and/or Y are identical or different and each represents hydrogen, hydroxyl, halogen or azido, and/or represent a 3- to 6-membered ring which may be saturated, unsaturated and/or partially unsaturated and may contain 1 to 3 heteroatoms from the group consisting of N, O, S, SO, $SO_2$, which may optionally contain a carbonyl group as ring member, which may also be attached via N and which is optionally mono- or polysubstituted by identical or different substituents from the group consisting of straight-chain or branched alkyl having up to 4 carbon atoms which is optionally substituted by hydroxyl, amino, halogen, carboxyl, straight-chain or branched acyl, alkoxy, alkoxycarbonyl or acylamino having in each case up to 4 carbon atoms, and/or represent straight-chain or branched acyl having up to 4 carbon atoms which is optionally substituted by halogen, or represent straight-chain or branched acyloxy having up to 4 carbon atoms, and/or represent radicals of the formulae $-SO_3H$ or $S(O)_cR^6$, in which c represents a number 1 or 2, $R^6$ represents straight-chain or branched alkyl having 1 to 8 carbon atoms, phenyl or a 5- to 6-membered heterocycle having up to 2 heteroatoms from the group consisting of S, N and O, where the ring systems may optionally be substituted by halogen or by straight-chain or branched alkyl or alkoxy having in each case up to 3 carbon atoms, and/or represent a radical of the formula $PO(OR^7)(OR^8)$, in which $R^7$ and $R^8$ are identical or different and each represents hydrogen, straight-chain or branched alkyl having up to 4 carbon atoms or cyclopropyl, cyclopentyl, phenyl or benzyl, and/or represent oxycycloalkyl having 3 to 6 carbon atoms or represent radicals of the formulae $-CON=C(NH_2)_2$ or $-C=NH(NH_2)$ or $(CO)_dNR^9R^{10}$ or $NHCONR^{12'}R^{13'}$, in which d represents a number 0 or 1, $R^9$ and $R^{10}$ are identical or different and each represent hydrogen, straight-chain or branched alkyl having up to 4 carbon atoms or cyclopropyl, cyclopentyl, cyclohexyl or phenyl, and in the case where d=0

$R^9$ and $R^{10}$ also represent straight-chain, branched or cyclic acyl having up to 5 carbon atoms, straight-chain or branched hydroxyalkyl having up to 3 carbon atoms, straight-chain or branched alkoxyalkyl having a total of up to 8 carbon atoms, straight-chain or branched alkoxy carbonyl or acyloxyalkyl having in each case up to 3 carbon atoms or a radical of the formula $-SO_2R^{11}$ or a radical of the formulae

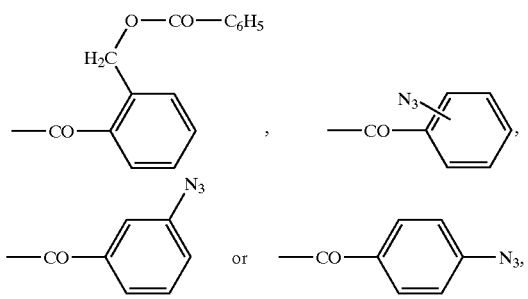

in which $R^{11}$ represents straight-chain or branched alkyl having up to 4 carbon atoms and/or $R^9$ and $R^{10}$ represent radicals of the formulae

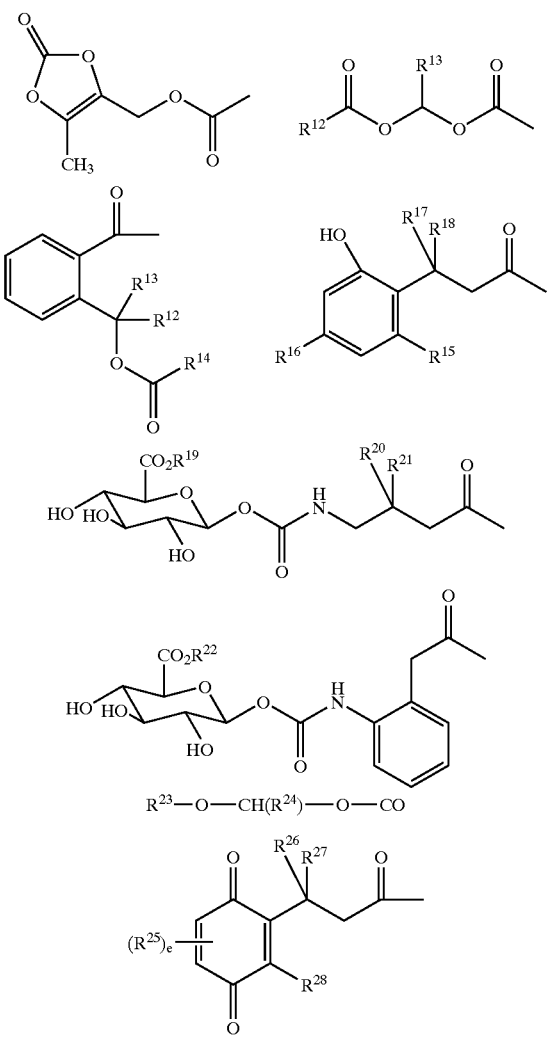

in which $R^{12}$, $R^{13}$ and $R^{15}$ to $R^{28}$ are identical or different and each represents hydrogen or straight-chain or branched alkyl having up to 4 carbon atoms, e represents a number 0, 1 or 2 and $R^{14}$ represents straight-chain or branched alkyl having up to 6 carbon atoms or cycloalkyl having 3 to 8 carbon atoms, $R^{9'}$ and $R^{10'}$ are identical or different and each represents hydrogen; alkyl having up to 4 carbon atoms which is optionally substituted by hydroxyl or alkoxy having up to 7 carbon atoms, phenyl which is optionally substituted by halogen, $R^2$ and $R^3$ form, together wvith the double bond, a phenyl, pyridyl or pyrimidinyl ring, A represents phenyl or pyrimidyl, each of which is optionally substituted by fluorine, chlorine or bromine, and their isomeric forms and salts.

In the compounds of the formula (I) according to the invention described above, the radicals $R^1$, X and Y are, according to a preferred embodiment, attached to the positions of the pyrimidine ring shown:

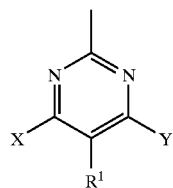

$R^1$ then preferably represents one of the abovementioned optionally substituted cycloalkyl or cycloalkenyl radicals, such as, for example, cyclopropyl, cyclobutyl, cyclopentenyl, cyclopentyl, cyclohexyl, 1-hydroxycyclopropyl and 1-(fluoromethyl)cyclopropyl; amongst these, cyclopropyl is particularly preferred.

X then represents, for example, an $NH_2$ group and

Y represents hydrogen or an $NH_2$ group.

In the compounds of the formula (I) according to the invention described above, $R^2$ and $R^3$ represent, according to a preferred embodiment and together with the double bond, a fused phenyl ring or a fused pyridyl ring, resulting in an indazole or a pyrazolo[3,4]-pyridine skeleton. Particular preference is given to a pyrazolo[3,4]-pyridine skeleton.

In the compounds of the formula (I) according to the invention described above, according to a preferred embodiment, the radical A represents a halogen-, in particular fluorine-, substituted phenyl ring. The substituent is preferably in the ortho-position to the methylene bridge.

In addition, processes for preparing compounds according to the invention of the general formula (I) have been found, characterized in that, depending on the various meanings of the heterocycles listed above under $R^2$ and $R^3$,

[A] Compounds of the General Formula (II)

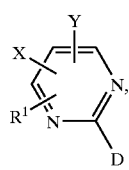

in which $R^1$, X and Y are each as defined above and

D represents radicals of the formulae

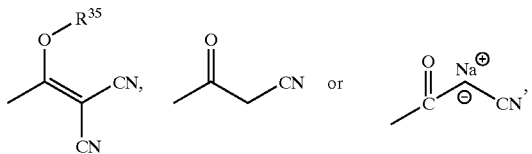

in which $R^{35}$ represents $C_1-C_4$-alkyl are converted, by reaction with compounds of the general formula (III)

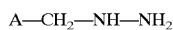

$$A-CH_2-NH-NH_2 \qquad (III),$$

in which

A is as defined above in inert solvents, if appropriate in the presence of a base, into the compounds of the general formula (IV) or (IVa)

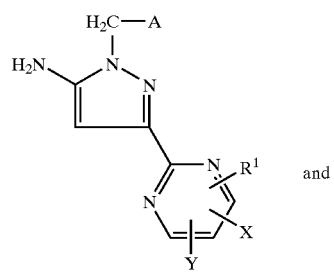

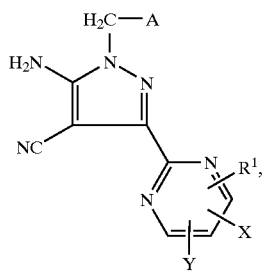

in which

A, X, Y and $R^1$ are each as defined above, and, in the case of the compounds of the general formula (IVa), are subsequently cyclized with carboxylic acids, nitrites, formamides or guanidium salts, and, in the case of the compounds of the general formula (IV), are cyclized with 1,3-dicarbonyl derivatives, their salts, tautomers, enol ethers or enanines, in the presence of acids and, if appropriate, under microwave irradiation, or

[B] in the case that $R^2$ and $R^3$ together form a pyrazine ring, compounds of the general formula (IV) are initially converted by nitrosation into the compounds of the general formula (V)

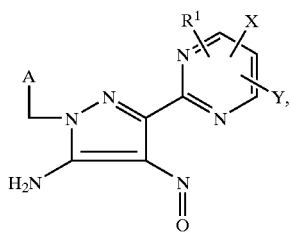

(V)

in which
A, X, Y and R$^1$ are each as defined above,
in a second step, the compounds of the general formula (VI)

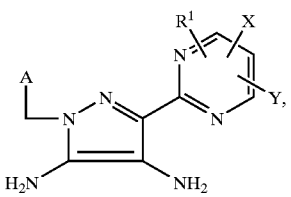

(VI)

in which
A, X, Y and R$^1$ are each as defined above are prepared by a reduction,
and these are subsequently cyclized with 1,2-dicarbonyl compounds, preferably aqueous glyoxal solution, or

[C] compounds of the general formula (VII)

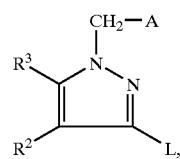

(VII)

in which
A$^1$, R$^2$ and R$^3$ are each as defined above and
L represents a radical of the formula —SnR$^{36}$R$^{37}$R$^{38}$, ZnR$^{39}$, iodine, bromine or triflate,
in which
R$^{36}$, R$^{37}$ and R$^{38}$ are identical or different and each represent straight-chain or branched alkyl having up to 4 carbon atoms and
R$^{39}$ represents halogen
are reacted with compounds of the general formula (VIII)

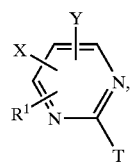

(VIII)

in which
X, Y and R$^1$ are each as defined above and
in the case that L=SnR$^{36}$R$^{37}$R$^{38}$ or ZnR$^{39}$,
T represents triflate or represents halogen, preferably bromine and,
in the case that L=iodine, bromine or triflate,
T represents a radical of the formula SnR$^{36'}$R$^{37'}$R$^{38'}$, ZnR$^{39'}$ or BR$^{40}$R$^{41}$, in which
R$^{36'}$, R$^{37'}$, R$^{38'}$ and R$^{39'}$ have the meanings of R$^{36}$, R$^{37}$, R$^{38}$ and R$^{39}$ given above and are identical to or different from them,
R$^{40}$ and R$^{41}$ are identical or different and each represent hydroxyl, aryloxy having 6 to 10 carbon atoms or straight-chain or branched alkyl or alkoxy having in each case up to 5 carbon atoms, or together form a 5- or 6-membered carbocyclic ring
in a palladium-catalysed reaction in inert solvents, if appropriate in the presence of a base, or

[D] amidines of the general formula (IX)

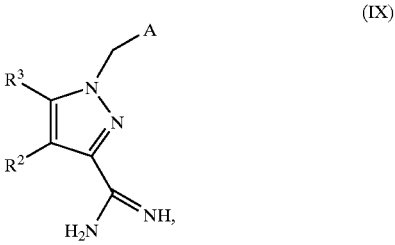

(IX)

in which
A, R$^2$ and R$^3$ are each as defined above
are reacted, for example, with compounds of the general formula (X), (Xa), (Xb) or (Xc)

(X)

NC—C(R$^{1'}$)=Z (Xa)

NC—CH(R$^{1'}$)—CN (Xb)

AlkOOC—CH(R$^{1'}$)—COOAlk (Xc)

AlkOOC—CH(R$^{1'}$)—CN in which
R$^{1'}$ represents the optionally substituted cycloalkyl radical listed above under R$^1$;
Alk represents straight-chain or branched alkyl having up to 8 carbon atoms, preferably up to four carbon atoms; and
Z represents an NH$_2$ group, a monoalkylamino group having up to 7 carbon atoms, a dialkylamino group having up to 7 carbon atoms, a piperidinyl or morpholinyl radical which is attached via the nitrogen, hydroxyl, alkoxy having up to 7 carbon atoms, acyloxy having up to 7 carbon atoms or aroyloxy having 6 to 10 carbon atoms,
and, if appropriate, the substituents listed under X, Y, R$^1$, R$^2$, R$^3$ and/or A are modified or introduced by customary methods, preferably by acylation and derivatization of free amino groups, chlorination, catalytic hydrogenation, reduction, oxidation, removal of protective groups and/or nucleophilic substitution.

The heterocycles listed under $R^2$ and $R^3$ can also be introduced by reacting the appropriately substituted compounds of the general formula (II) according to other known heterocyclic syntheses.

The process [D] according to the invention can be illustrated by the following embodiment:

[D]

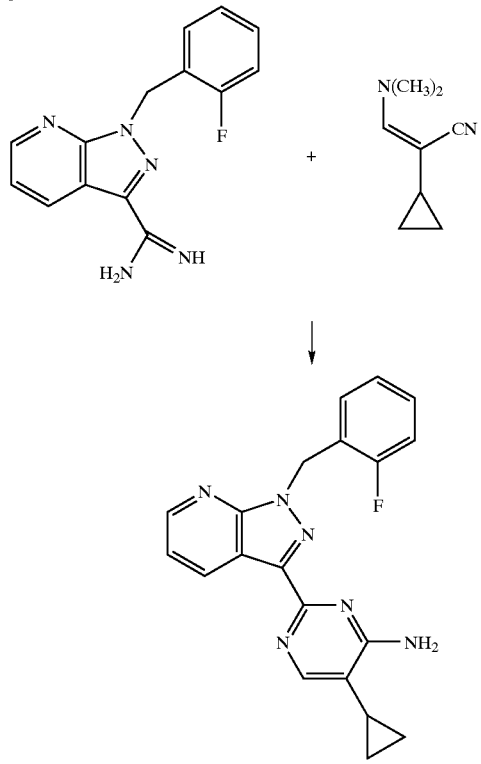

Suitable solvents for the individual steps of process [A] and [B] are inert organic solvents which do not change under the reaction conditions. These include ethers, such as diethyl ether or tetrahydrofuran, DME, dioxane, alcohols, such as methanol and ethanol, halogenated hydrocarbons, such as dichloromethane, trichloromethane, carbon tetrachloride, 1,2-dichloroethane, trichloroethane, tetrachloroethane, 1,2-dichloro-ethylene or trichloroethylene, hydrocarbons, such as benzene, xylene, toluene, hexane, cyclohexane, or mineral oil fractions, nitromethane, dimethylformamide, acetone, acetonitrile or hexamethylphosphoric triamide. It is also possible to use mixtures of the solvents. Particular preference is given to tetrahydrofuran, dimethylformamide, toluene, dioxane or dimethoxyethane.

Bases which are suitable for use in the processes according to the invention are, in general, inorganic or organic bases. These preferably include alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or alkali metal or alkaline earth metal alkoxides, such as sodium methoxide or potassium methoxide, sodium ethoxide or potassium ethoxide or potassium tert-butoxide, or organic amines (trialkyl($C_1$–$C_6$)-amines), such as triethylamine, or heterocycles, such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to use alkali metals, such as sodium, and their hydrides, such as sodium hydride, as bases. Preference is given to sodium carbonate and potassium carbonate, triethylamine and sodium hydride.

When reacting the compounds of the formula (II) with the compounds of the formula (III), the base is employed in an amount of from 1 mol to 5 mol, preferably from 1 mol to 3 mol, based on 1 mol of the compound of the general formula (II).

The reaction of the compounds of the formula (II) with the compounds of the formula (III) is generally carried out in a temperature range of from 0° C. to 150° C., preferably from +20° C. to +110° C.

This reaction can be carried out at atmospheric pressure or at elevated or reduced pressure (for example from 0.5 to 5 bar). In general, the reaction is carried out at atmospheric pressure.

Suitable acids for the cyclization reactions which may have to be carried out in the processes according to the invention are, in general, protic acids. These preferably include inorganic acids, such as, for example, hydrochloric acid or sulphuric acid, or organic carboxylic acids having 1–6 C atoms which are optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or aryl radicals, such as, for example, methanesulphonic acid, ethanesulphonic acid, benzenesulphonic acid or toluenesulphonic acid.

The catalytic hydrogenation reactions which may have to be carried out in the processes according to the invention can generally be carried out with hydrogen in water or in inert organic solvents, such as alcohols, ethers or halogenated hydrocarbons, or mixtures thereof, using catalysts such as raney nickel, palladium, palladium on animal charcoal or platinum, or using hydrides or boranes in inert solvents, if appropriate in the presence of a catalyst.

The chlorination reactions which may have to be carried out in the processes according to the invention are generally carried out using the customary chlorinating agents, such as, for example, $PCl_3$, $PCl_5$, $POCl_3$ or elemental chlorine. In the context of the invention, preference is given to $POCl_3$.

The acylations and derivatizations of free amino groups which may have to be carried out in the processes according to the invention can be carried out by customary methods which are known to the person skilled in the art. It is possible, for example, to convert appropriate free amino groups by reaction with an acyl halide, preferably an acyl chloride, or an acetic anhydride, in the presence of a base, such as, for example, sodium hydride, pyridine or dimethylaminopyridine in a solvent such as tetrahydrofuran or dichloromethane into the respective amides, by reaction with an appropriate aldehyde in a solvent such as ethanol or acetonitrile into the respective N,O-hemiacetals or N,O-acetals by reaction with a sulphonyl halide, preferably a sulphonyl chloride, into the respective sulphonamides, by reaction with a chloroformic ester into the respective urethanes or by reaction with an isocyanate in a solvent such as dichloromethane into the respective urea derivatives.

The nucleophilic substitutions and Vilsmeier reactions which may have to be carried out in the processes according to the invention are carried out by customary methods known to the person skilled in the art.

The nitrosation of the compounds of the formula (IV) to the compounds of the formula (V), which constitutes the first step of the process [B], can be carried out in accordance with the procedure of P. G. Baraldi et al., Synthesis 1984, 148.

The reductions which may have to be carried out in the processes according to the invention are generally carried out using reducing agents, preferably those which are suitable for reducing carbonyl to hydroxyl compounds. Particularly suitable here is the reduction with metal hydrides or complex metal hydrides in inert solvents, if appropriate in the presence of a trialkylborane. Preference is given to reduction with complex metal hydrides, such as, for example, lithium borohydride, sodium borohydride, potassium borohydride, zinc borohydride, lithium trialkyl borohydride, diisobutylaluminium hydride or lithium aluminium hydride. The reduction is very particularly preferably carried out using diisobutylaluminium hydride and sodium borohydride.

Here, the reducing agent is generally employed in an amount of from 1 mol to 6 mol, preferably from 1 mol to 4 mol, based on 1 mol of the compounds to be reduced.

The reductions which may have to be carried out in the processes according to the invention are generally carried out in a temperature range of from −78° C. to +50° C., preferably from −78° C. to 0° C. in the case of DIBAH and 0° C. to room temperature in the case of $NaBH_4$.

The reductions which may have to be carried out in the processes according to the invention are generally carried out at atmospheric pressure. However, it is also possible to operate under elevated or reduced pressure.

The compounds of the general formulae (II) and (III) are known per se, or they can be prepared by customary methods (cf.: J. Hromatha et al., Monatsh. Chem. 1976, 107, 233).

Some of the compounds of the general formulae (IV), (IVa), (V) and (VI) are known, and they can be prepared as described above.

Suitable solvents for the process [C] are inert organic solvents which do not change under the reaction conditions. These include ethers, such as diethyl ether or tetrahydrofuran, DME, dioxane, halogenated hydrocarbons, such as dichloromethane, trichloromethane, carbon tetrachloride, 1,2-dichloroethane, trichloroethane, tetrachloroethane, 1,2-dichloroethylene or trichloroethylene, hydrocarbons, such as benzene, xylene, toluene, hexane, cyclohexane, or mineral oil fractions, nitromethane, dimethylformamide, acetone, acetonitrile or hexamethylphosphoric triamide. It is also possible to use mixtures of the solvents. Particular preference is given to tetrahydrofuran, dimethylformamide, toluene, dioxane or dimethoxyethane.

The reaction of the compounds of the formula (VII) with the compounds of the formula (VIII) is generally carried out in a temperature range of from 0° C. to 150° C., preferably from +20° C. to +110° C.

This reaction can be carried out at atmospheric pressure or at elevated or reduced pressure (for example from 0.5 to 5 bar). In general, the reaction is carried out at atmospheric pressure.

Suitable palladium compounds in the context of the present invention are, in general, $PdCl_2(P(C_6H_5)_3)_2$, palladium-bis-dibenzylideneacetone $(Pd(dba)_2)$, [1,1'-bis-(diphenylphosphino)ferrocene]-palladium(II) chloride (Pd $(dppf)Cl_2$) or $Pd(P(C_6H_5)_3)_4$. Preference is given to $Pd(P(C_6H_5)_3)_4$.

The compounds of the general formula (VII) are known per se, or they can be prepared by customary methods (cf., for example K. Kirschke in: Houben-Weyl, Methoden der organischen Chemie, Thieme-Verlag Stuttgart, 4th Ed., volume E8b, part 2, 399–763; in particular with respect to pyrazolopyridines: C. R. Hardy in A. R. Katritzky (Ed.), Adv. Het. Chem. 1984, 36, 343–409; in particular with respect to pyrazolopyrimidines:

M. H. Elgnadi et at., Adv. Het. Chem. 1987, 41, 319–376). The preparation of the corresponding halogenopyrozolo[3, 4-b]pyrimidines and organotin pyrazolo[3,4-b]pyrimidines of the formula (VII) is described in WO 98/23619 and can also be carried out analogously for the corresponding triflate and organotin compounds of the formula (VII).

The compounds of the general formula (VIII) are known and can be prepared by customary methods (cf, for example, M. G. Hoffmann et al. in: Houben-Weyl, Methoden der organischen Chemie, 4th ed., volume E9b, part 1, pp. 1–249; A. Weissenberger et al., The Chemistry of heterocyclic compounds—pyrimidines, 1962, 16; ibid 1970, 16, suppl. 1, ibid 1985, 16, suppl. 2; ibid 1994, 52).

The process [D] is carried out in a temperature range of from 80° C. to 120° C., preferably at from 100° C. to 110° C., or under reflux.

Suitable solvents are, for example, the reagents of the general formula (X), (Xa), (Xb) or (Xc). However, the reaction can also be carried out in other suitable solvents, such as, for example, toluene, methanol or dichloromethane. Low-boiling solvents, such as, for example, dichloromethane, can be distilled off during the course of the reaction.

The process [D] can be carried out at atmospheric pressure or at elevated or reduced pressure (for example from 0.5 to 5 bar). In general, the process is carried out at atmospheric pressure.

The amidines of the general formula (IX) are novel and are therefore a further subject of the invention. They can be prepared by reacting the compounds of the general formula (XI)

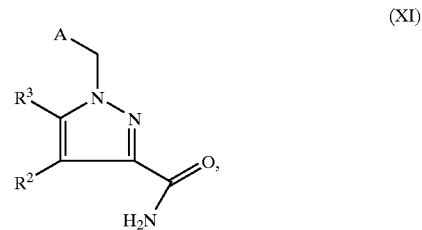

(XI)

in which

A, $R^2$ and $R^3$ are each as defined above initially in ethers with trifluoroacetic anhydride (TFAA) and in the presence of bases to give the compound of the general formula (XII)

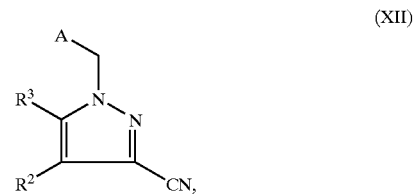

(XII)

in which

A, $R^2$ and $R^3$ are each as defined above, subsequently preparing the compounds of the general formula (XIII)

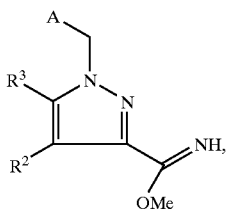
(XIII)

in which

A, $R^2$ and $R^3$ are each as defined above
using sodium methoxide, in a next step converting these compounds by reaction with $NH_4Cl$ and glacial acetic acid in alcohols into the corresponding amidine HCl salt of the general formula (XIV)

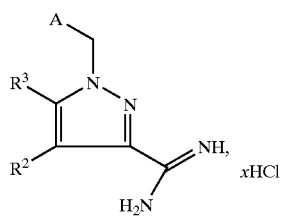
(XIV)

in which

A, $R^2$ and $R^3$ are each as defined above
and, in a last step, reacting with bases, preferably sodium carbonate, or alkali metal alkoxide, such as sodium ethoxide.

Suitable solvents for reacting the compounds of the general formula (XI) to give the compounds of the formula (XII) are ethers, such as diethyl ether or tetrahydrofuran, dimethylformamide and dioxane; preference is given to tetrahydrofuran.

Suitable for use as bases here are organic amines (trialkyl ($C_1$–$C_6$)-amines) such as triethylamine, or heterocycles, such as 1,4-diazabicyclo[2.2.2]octane (DABCO), 1,8-diazabicyclo[5.4.0]undec-7-ene (DBU), pyridine, dimethylaminopyridine, methylpiperidine or morpholine. Preference is given to pyridine.

The reaction is carried out in a temperature range of from 0° C. to 40° C., preferably at room temperature.

The reaction can be carried out at atmospheric pressure or at elevated or reduced pressure (for example from 0.5 to 5 bar). In general, the reaction is carried out at atmospheric pressure.

The amide (XI) can be prepared, for example, by hydrolysing an appropriate ester as starting material with a base to give the acid, converting the acid into the acyl chloride by customary methods, for example using $SOCl_2$ or $POCl_3$, followed by reaction with ammonia.

The elimination of water from the amide (XI) to given the nitrile (XII) can be carried out with any customary dehydrating agent. Preference according to the invention is given to trifluoroacetic anhydride (TFAA).

The nitrile of the formula (XII) can be converted into the iminoether of the formula (XIII) both under acidic conditions, such as, for example, with HCl/alcohol mixtures, and under basic conditions, such as, for example, with methanol/sodium methoxide. It is generally carried out at from 0° C. to 40° C., for example at room temperature.

Suitable solvents for converting the compounds of the general formula (XIII) into the compounds of the formula (XIV) are alcohols, such as methanol or ethanol. Preference is given to methanol.

The reaction is carried out in a temperature range of from 0° C. to 40° C., preferably at room temperature.

The reaction can be carried out under atmospheric pressure or under elevated or reduced pressure (for example from 0.5 to 5 bar). In general, the reaction is carried out at atmospheric pressure.

Suitable bases for liberating the compounds of the general formula (IX) from compounds of the general formula (XIV) are inorganic or organic bases. These include, for example, alkali metal hydroxides, such as sodium hydroxide or potassium hydroxide, alkaline earth metal hydroxides, such as barium hydroxide, alkali metal carbonates, such as sodium carbonate or potassium carbonate, alkaline earth metal carbonates, such as calcium carbonate, and alkali metal alkoxides, such as sodium methoxide. Preference is given to sodium carbonate and sodium methoxide.

The pyrimidine ring is prepared by customary methods (cf., for example, M. G. Hoffmann et al. in: Houben-Weyl, Methoden der organischen Chemie, 4th ed., volume E9b, part 1, pp. 1–249; A. Weissenberger et al., The Chemistry of heterocyclic compounds—pyrimidines, 1962, 16; ibid 1970, 16, suppl. 1, ibid 1985, 16, suppl. 2; ibid 1994, 52).

Here, the iminoethers of the formula (XIII) can be used as starting materials and be reacted, for example, with a suitable enamine. However, it is also possible to convert the iminoether first, using ammonia or its salts, into a corresponding amidine and to react this either as the free base (IX) or as a salt (XIV) with enamines, acetals, enol ethers, aldehydes, enolates, malononitrile esters or malonodinitriles.

The enamines which may have to be used in this reaction can be prepared, for example, from C-H-acidic compounds, such as acetonitrile derivatives, according to known methods, by reaction with dimethylformamide derivatives, such as, for example, bis(dimethylamino)-tert-butoxymethane, dialkoxy-dialkylamino-methanes.

The compounds of the general formula (XI) are novel and are therefore a further subject of the invention. They can be prepared by converting the compounds of the general formula (XV)

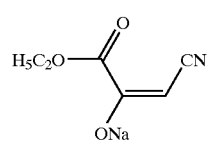
(XV)

with the compounds of the general formula (XVI)

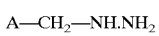
(XVI)

in ethers, preferably dioxane, and trifluoroacetic acid into the compounds of the general formula (XVII)

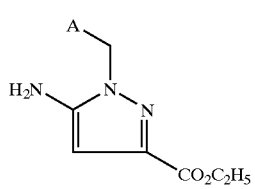
(XVII)

subsequently preparing, by reaction with the compounds of the general formula (XVIII)

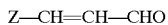 (XVIII)

in which
Z is as defined above, in particular —N(CH$_3$)$_2$
in inert solvents, preferably dioxane, the compounds of the general formula (XIX)

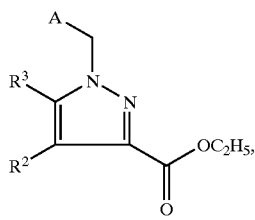 (XIX)

followed in a last step by treatment with ammonia in methanol.

Instead of the sodium salt of the enolate (XV), it is also possible to employ enol ethers, ketones or enamines.

If appropriate, the reaction of the compounds of the general formulae (XV) and (XVI) to give (XVII) can also be carried out via intermediates of the formulae (A) and (B), which are likewise novel,

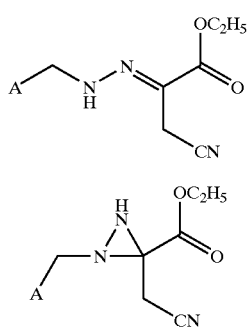

at room temperature. These represent, therefore, a further subject of the invention.

The compounds of the general formula (X) are novel and can be prepared, for example, by reacting the compounds of the formula (XX) or (XXa)

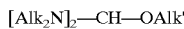 (XX)

 (XXa)

in which
Alk and Alk' are identical or different and each represent straight-chain or branched alkyl having up to 5 carbon atoms
with compounds of the formula (XXI)

 (XXI)

in which
R$^{1'}$ represents the cycloalkyl radical listed above under R$^1$.

The compounds of the general formulae (XX), (XXa) and (XXI) are known, or they can be prepared by customary methods.

Some of the compounds of the general formulae (XII), (XIII), (XIV), (XV), (XVII), (XVIII) and (XIX) are novel, and they can be prepared as described above.

The pyrimidine radical can also be synthesized with the aid of the reagent of the formula (Xa) which is accessible, for example, as follows:
Compounds of the general formula

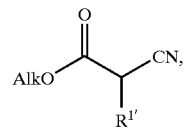 (XXII)

in which
R$^{1'}$ is as defined above and Alk represents an alkyl radical having up to 4 carbon atoms
are converted, by using ammonia in suitable solvents, preferably alcohols such as methanol, at temperatures from 0° C. to 40° C., preferably at room temperature, into compounds of the general formula (XXII)

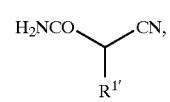 (XXIII)

in which R$^{1'}$ is as defined above,
and these are subsequently reacted by customary methods with dehydrating agents, such as, for example, Burgess reagent, POCl$_3$, P$_2$O$_5$, SOCl$_2$, trifluoroacetic anhydride/pyridine.

If Burgess reagent is used, the reaction is preferably carried out in inert solvents, such as ethers or chlorinated hydrocarbons. Examples which may be mentioned are dichloromethane and tetrahydrofuran. Preference is given to using a 1:2 mixture of the abovementioned solvents. The reaction is carried out at temperatures from 0° C. to 40° C., preferably at room temperature.

The compounds of the formula (XXII) are known and/or obtainable in a simple manner known to the person skilled in the art.

Some of the compounds of the formula (X) undergo keto-enol tautomerism, for example:

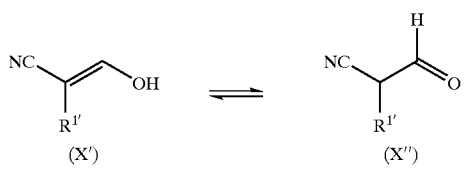

If R$^2$ and R$^3$ together with the double bond form a phenyl ring, the corresponding 3-cyano-indazoles are reacted with compounds of the general formula (XXIV)

 (XXIV)

in which
A is as defined above and
Hal represents Cl, Br or I, preferably Br,
in inert solvents, preferably with tetrahydrofuran in the presence of a base, preferably sodium hydride, to give the compounds of the general formula (XXV)

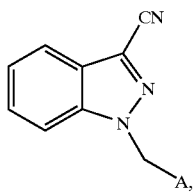

(XXV)

in which

A is as defined above which are subsequently treated with ammonium chloride and sodium methoxide as described above.

The compounds of the general formula (XXIV) are known, or they can be prepared by customary methods.

The compounds of the general formula (XXV) are novel and can be prepared as described above.

The compounds of the general formula (I) according to the invention have an unforeseeable, valuable spectrum of pharmacological action.

The compounds of the general formula (I) according to the invention lead to a vasorelaxation, inhibition of platelet aggregation and to a fall in blood pressure and also to an increase in coronary blood flow. These actions are mediated via a direct stimulation of soluble guanylate cyclase and an intracellular cGMP increase. Additionally, the compounds of the general formula (I) according to the invention enhance the action of substances which raise the cGMP level, such as, for example, EDRF (endothelium-derived relaxing factor), NO donors, protoporphyrin IX, arachidonic acid or phenylhydrazine derivatives.

They can therefore be employed in medicaments for the treatment of cardiovascular disorders, such as, for example, for the treatment of high blood pressure and cardiac insufficiency, stable and unstable angina pectoris, peripheral and cardiac vascular disorders, arrhythmias, for the treatment of thromboembolic disorders and ischaemias such as myocardial infarct, stroke, transitory and ischaemic attacks, peripheral circulatory disorders, prevention of restenoses such as after thrombolysis therapy, percutaneous translumino angioplastie (PTA), percutaneous transluminalo coronary angioplasty (PTCA), bypass and also for the treatment of arteriosclerosis, asthmatic disorders and disorders of the urogenital system such as, for example, prostate hypertrophy, erectile dysfunction, female sexual dysfunction and incontinence.

The compounds of the general formula (I) described in the present invention are also active compounds for controlling disorders in the central nervous system which are characterized by disturbances of the NO/cGMP system. In particular, they are suitable for eliminating cognitive deficits, for improving learning and memory performance and for treating Alzheimer's disease. They are also suitable for the treatment of disorders of the central nervous system such as states of anxiety, tension and depression, sleeping disorders and sexual dysfunction caused by the central nervous system, and for regulating pathological eating disorders or disorders associated with the use of stimulants and drugs.

Furthermore, the active compounds are also suitable for regulating cerebral circulation, and they are therefore effective agents for controlling migraines.

They are also suitable for the prophylaxis and control of the sequelae of cerebral infarcts (Apoplexia cerebri) such as stroke, cerebral ischaemia and skull-brain trauma. The compounds of the general formula (I) according to the invention can also be employed for controlling pain.

Additionally, the compounds according to the invention have antiinflammatory action and can therefore be employed as antiinflammatories.

The invention moreover includes the combination of the compounds of the general formula (I) according to the invention with organic nitrates and NO donors.

Organic nitrates and NO donors in the context of the invention are, in general, substances which display their therapeutic action by the release of NO or NO species. Sodium nitroprusside, glycerol trinitrate, isosorbide dinitrate, isosorbide mononitrate, molsidomine and SIN-1 are preferred.

The invention additionally includes the combination with compounds which inhibit the degradation of cyclic guanosine monophosphate (cGMP). These are, in particular, inhibitors of phosphodiesterases 1, 2 and 5; nomenclature according to Beavo and Reifsnyder (1990) TiPS 11 p. 150 to 155. The action of the compound according to the invention is potentiated and the desired pharmacological effect is increased by these inhibitors.

To determine the cardiovascular action, the following investigations were carried out: In in vitro investigations on the isolated enzyme and on cells of vascular origin, the effect on guanylate cyclase-dependent cGMP formation was tested with and without NO donor. The anti-aggregatory properties were shown on human platelets stimulated with collagen. The vasorelaxant action was determined in rabbit aortal rings preconcentrated with phenylephrine. The hypotensive action was investigated in anaesthetized and awake rats.

Stimulation of Recombinant Soluble Guanylate Cyclase in vitro

The investigations on the stimulation of recombinant soluble guanylate cyclase by the compounds according to the invention with and without NO donor were carried out using the method which is described in detail in the following literature reference: M. Hoenicka, E. M. Becker, H. Apeler, T. Sirichoke, H. Schroeder, R. Gerzer and J.-P. Stasch: Purified soluble guanylate cyclase expressed in a baculovirus/Sf9 system: stimulation by YC-1, nitric oxide, and carbon oxide. J. Mol. Med. 77: 14–23 (1999). The results are shown in FIG. 1.

Stimulation of Soluble Guanylate Cyclase in Primary Endothelial Cells

Primary endothelial cells were isolated from pig aortas by treatment with collagenase soln. The cells were then cultured in culture medium at 37□ C./5% $CO_2$ until confluence was reached. For the investigations, the cells were passaged, inoculated into 24-well cell culture plates and subcultured until reaching confluence (~2×10$^5$ cells/well). For the stimulation of endothelial guanylate cyclase, the culture medium was aspirated and the cells were washed once with Ringer solution. After removing the Ringer solution, the cells were incubated for 10 minutes, at 37° C./5% $CO_2$ in stimulation buffer. Following this, the test substances (final concentration 1 $\mu$M) were added to the cells by pipette. After a further 10 minutes the buffer solution was aspirated and cold buffer at 4° C. was added to the cells. The cells were then lysed at −20° C. for 16 hours. The supernatants containing the intracellular cGMP were then removed and the cGMP concentration was determined by means of the cGMP-SPA system (Amersham Buchler, Brunswick). The results are shown in Table 1.

TABLE 1

| Ex. No. | Concentration ($\mu$M) | 0 | 0.1 | 0.3 | 1.0 | 3.0 | 10 |
|---|---|---|---|---|---|---|---|
| 1 | cGMP (pmol/well) | 1.4 | 2.2 | 4.0 | 6.9 | 8.5 | 14.6 |

Vasorelaxant Action in vitro

Rabbits are anaesthetized by a blow to the neck and exanguinated. The aorta is removed, freed from adhering tissue, divided into 1.5 mm wide rings and individually transferred under a pretension into 5 ml organ baths containing a warm, carbogen-aerated Krebs-Henseleit solution at 37° C. of the following composition (mM): NaCl: 119; KCl: 4.8; $CaCl_2 \times 2\ H_2O$: 1; $MgSO_4 \times 7\ H_2O$: 1.4; $KH_2PO_4$: 1.2; $NaHCO_3$: 25; glucose: 10. The contractility is detected using Statham UC2 cells, amplified and digitalized by means of A/D converters (DAS-1802 HC, Keithley Instruments Munich), and recorded in parallel on linear recorders. To produce a contraction, phenylephrin is added to the bath cumulatively in increasing concentration. After several control cycles, the substance to be investigated is investigated in each further passage in increasing dosage in each case, and the height of the contraction is compared with the height of the contraction achieved in the last preliminary passage. From this, the concentration which is necessary in order to reduce the height of the control value by 50% ($IC_{50}$) is calculated. The standard administration volume is 5 $\mu$l, and the proportion of DMSO in the bath solution corresponds to 0.1%. The results are shown in Table 2.

TABLE 2

| Example No. | $IC_{50}$ [$\mu$M] |
|---|---|
| 1 | 0.2 $\mu$M |

Blood Pressure Measurements in Anaesthetized Rats

Male Wistar rats having a bodyweight of 300–350 g are anaesthetized with Thiopental (100 mg/kg i.p.). After tracheotomy, a catheter is inserted into the femoral artery for blood pressure measurement. The substances to be tested are administered orally in Transcutol, Cremophor EL, $H_2O$ (10%/20%/70%) in a volume of 1 ml/kg. The results are listed in Table 3 below.

TABLE 3

| Ex. No. | Dose (mg/kg p.o.) | Max. reduction in blood pressure (mm Hg) | Time (min) |
|---|---|---|---|
| 1 | 1 | 23 | 20 |
| 1 | 3 | 37 | 40 |

Effect on the Average Blood Pressure of Awake, Spontaneously Hypertensive Rats

Continuous measurements of blood pressure over 24 hours were carried out on spontaneously hypertensive female rats (MOL:SPRD) having a bodyweight of 200–250 g which were allowed to move around freely. To this end, pressure monitors (Data Sciences Inc., St. Paul, Minn., USA) were chronically implanted into the descending abdominal aorta of the animals, below the kidney artery, and the attached transmitter was fixed in the abdominal cavity.

The animals were kept individually in type III cages, which were positioned on the individual receiver stations, and adapted to a 12-hour day/night rhythm. Water and feed was available freely.

To collect the data, the blood pressure of each rat was registered every 5 minutes for 10 seconds. In each case, the data for a period of 15 minutes were collected and the average value was calculated from these values.

Figure 2:
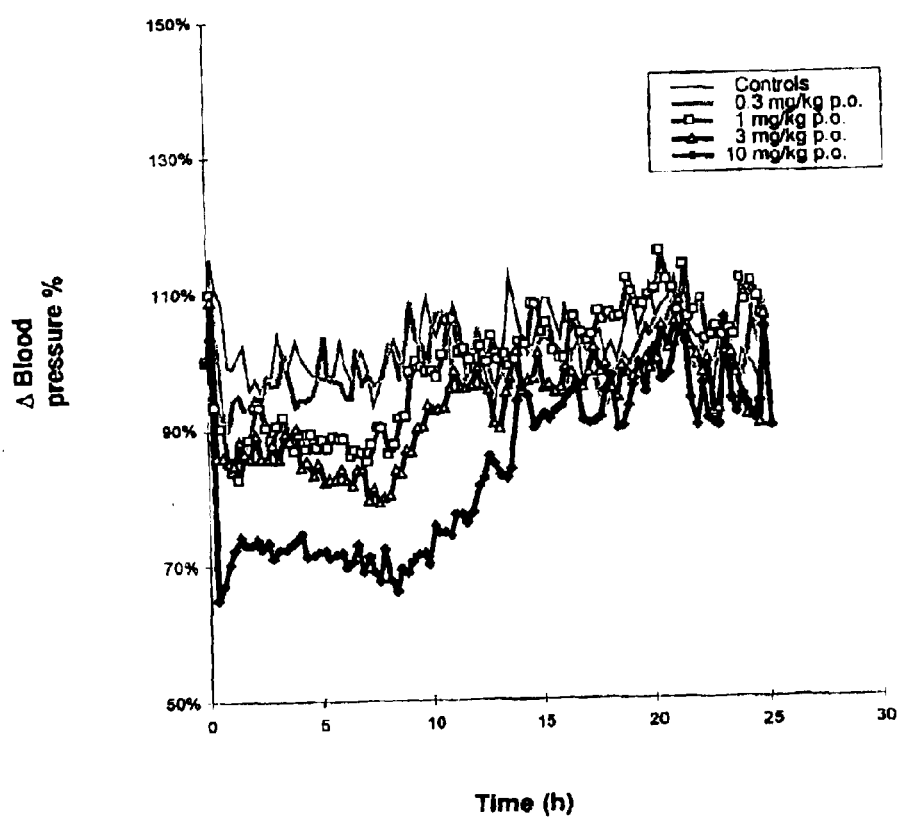
FIG. 2 shows the effect of 3-(4-amino-5-cyclopropyl-pyrimidin-2-yl)-1-(2-fluorobenzyl)1H-pyrazolo-[3,4-b]-pyridine (Example 1) on the average blood pressure of awake, spontaneously hypertensive rats.

The compounds to be tested were dissolved in a mixture of Transcutol (10%), Cremophor (20%), $H_2O$ (70%) and administered orally by means of a stomach tube in a volume of 2 ml/kg of bodyweight. The doses tested were between 0.3 and 30 mg/kg of bodyweight. The results are shown in FIG. 2.

Inhibition of Platelet Aggregation in vitro

To determine the platelet-aggregation, blood from healthy volunteers of both sexes was used. As an anticoagulant, 9 parts of blood were admixed to one part of 3.8% strength sodium citrate solution. The blood was centrifuged at 900 rpm for 20 min. The pH of the platelet-rich plasma obtained was adjusted to pH 6.5 using ACD solution (sodium citrate/citric acid/glucose). The platelets were subsequently centrifuged off and resuspended in buffer and once more centrifuged off. The platelet pellet was suspended in buffer and mixed with an additional 2 mmol/l of $CaCl_2$.

To measure the aggregation, aliquots of the platelet suspension were incubated with the substance to tested at 37° C. for 10 min. Aggregation was subsequently induced in an aggregometer by addition of collagen and determined at 37° C. using the turbidometric method according to Born (Born, G. V. R., J. Physiol. (London), 168, 178–195, 1963). The results are shown in Table 4 below.

TABLE 4

| Ex. No. | $IC_{50}$ ($\mu$M) |
|---|---|
| 1 | 0.003 |

Measurement of the Erection-promoting Action of Guanylate Cyclase Stimulators

For a complete and lasting erection to occur, the cavernous arteries and the entire cavernous body architecture, which is formed by a network of smooth muscle cells and collagen connective tissue, has to be at maximum dilation so that the corpus cavernosum can fill completely with blood (Anderson K.-E. and Wagner G., "Physiology of Penile Erection.". *Physiological Reviews* 75, 191–236 (1995); Meinhardt W. Kropmann R F, Vermeig P, Lycclama a Nigelholt and Zwartendijk J. "The Influence of Medication on Erectile dysfunction." *Int. J. of Impotence Res.* 9, 17–26 (1997). Relaxation of smooth muscles is mediated by NO which, in the case of sexual stimulation, is released by non-adrenergic, non-cholinergic nerve fibres in the endothelial cells of the blood vessels of the corpus cavernosum. NO activates guanylate cyclase, and the resulting increase in cGMP leads to dilation of the smooth muscles of the corpus cavernosum and consequently to an erection. To test the efficacy of the substances according to the invention, awake rabbits were used. The species rabbit was chosen since neurophysiology, haemodynamic and the control of contraction and relaxation of the smooth muscles of the corpus cavernosum of rabbit and man are quite similar (Meyer M F, Taher H., Krah H., Staubesand J., Becker A J, Kircher M, Mayer B., Jonas U., Forsmann W G., Stief Ch.G. "Intracavenous Application of SIN-1 in Rabbit and Man: Functional and Toxcological Results." *Annals Urol.* 27, 179–182 (1993); Taub H C, Lerner S E, Melman A, Christ G J "Relationship between contraction and relaxation in human and rabbit corpus cavernosum." *Urology* 42, 698–671, (1993).

Method

Adult male chinchilla rabbits having a weight of 3–5 kg are, after delivery, adapted for several days in isolation. They have free access to water and can feed for two hours per day. The animals are kept in a 10/14 hour day/night rhythm (light switched on from 8.00 hours onwards). The room temperature is 22–24° C.

The animals are weighed directly before the start of the experiment. For intravenous administration, the substances according to the invention were dissolved in a mixture of Transcutol (GATTEFOSSE GmbH) diluted with 20% Cremophor (BASF) and water in a ratio of 3/7. Sodium nitroprusside was dissolved in 0.9% NaCl. The substances were injected at the dosages stated in the table in a volume of 0.5 ml/kg into the auricular vein. For oral administration, the test substances were dissolved in a mixture of glycerol: water: polyethylene glycol 6:10:9.69 and administered at the dosages stated in the table in a volume of 1 ml/kg using the stomach tube.

The effect of guanylate cyclase stimulators is increased by NO donors. This was by demonstrated by additionally administering sodium nitroprusside.

The sodium nitroprusside was injected into the auricular vein at a dosage of 0.2 mg/kg simultaneously with the substance according to the invention. If the substance according to the invention was administered orally, the sodium nitroprusside was injected into the auricular vein of these animals 30 min after the oral administration. Corresponding controls were carried out using the solvent and using sodium nitroprusside on its own.

At rest, the penis of the rabbit is not visible in the pubic region and is covered completely by the sheath. The erection is assessed by measuring the length of the protruding penis with a calliper square. Measurements are carried out 5, 10, 15, 30, 45, 60, 120 and 180 min. after the administration of the substance. The effect is calculated as the product of the length of the penis which is not covered by fur in [mm] and the time for which the erection persists in [min].

Intravenous injection of sodium nitroprusside causes an erection which lasts for approximately 10 min. (110 [mm× min]).

TABLE 5

Erection-promoting effect of guanylate cyclase stimulators
(Unit: [mm] × [min])

| Substance | Dose i.v. | +SNP i.v. | +SNP i.v. | Dope po | +SNP po | −SNP po |
|---|---|---|---|---|---|---|
| Ex. 1 | 0.3 mg/kg | 140 | 0 | 1 mg/kg | 184 | ng |
| | 1 mg/kg | 369 | 184 | 3 mg/kg | 233 | ng |
| | | | | 10 mg/kg | 375 | ng |
| | | | | 30 mg/kg | 804 | 418 |
| Ex. 25 | 0.3 mg/kg | 85 | 0 | 3 mg/kg | 168 | ng |
| | 1 mg/kg | 245 | 0 | 10 mg/kg | 506 | ng |

Remarks

The substances were administered in the dosages stated. The sodium nitroprusside was in each case administered i.v., at 0.2 mg/kg. If the substance according to the invention was administered i.v., the sodium nitroprusside was administered simultaneously, if the substance according to the invention was administered orally, it was administered 30 min later. Sodium nitroprusside on its own has an effect of 100 [mm]×[min].

The present invention includes pharmaceutical preparations which, in addition to non-toxic, inert pharmaceutically acceptable excipients, contain the compounds of the general formula (I) according to the invention, and also processes for the production of these preparations.

The active compounds can optionally be present in one or more of the excipients indicated above and also in microencapsulated form.

The therapeutically active compounds of the general formula (I) should be present in the abovementioned pharmaceutical preparations in a concentration from approximately 0.1 to 99.5, preferably from approximately 0.5 to 95, % by weight of the total mixture.

In addition to the compounds of the general formula (I) according to the invention, the abovementioned pharmaceutical preparations can also contain other pharmaceutically active compounds.

In general, it has proved advantageous both in human and in veterinary medicine to administer the active compound(s) according to the invention in total amounts from approximately 0.5 to approximately 500, preferably 5 to 100, mg/kg of bodyweight every 24 hours, if appropriate in the form of several individual doses, to achieve the desired results. An individual dose contains the active compound(s) according to the invention preferably in amounts from approximately 1 to approximately 80, in particular 3 to 30, mg/kg of bodyweight.

Below, the present invention is illustrated in more detail using non-limiting, preferred examples. Unless indicated otherwise, all amounts given refer to per cent by weight.

EXAMPLES

Abbreviations

RT: Room temperature

EA: Ethyl acetate

BABA: n-Butyl acetate/n-butanol/glacial acetic acid/ phosphate buffer pH 6 (50:9:25:15; org. phase)

Mobile Phases for Thin-layer Chromatography

T1 E1: toluene/ethyl acetate (1:1)

T1 EtOH1: toluene-methanol (1:1)

C1 E1: cyclohexane/ethyl acetate (1:1)

C1 E2: cyclohexane/ethyl acetate (1:2)

Starting Materials

Example I

Cyclopropyl-3-oxopropionitrile

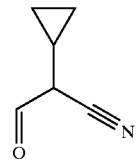

Under argon, 65.4 g (0.583 mol) of potassium tert-butoxide are dissolved in 400 ml of THF. At room temperature, a solution of 21.5 g (0.265 mol) of cyclopropylacetonitrile and 43.2 g (0.58 mol) of ethyl formate in 100 ml of THF is added. The mixture is stirred at RT for 3 hours. The THF is stripped off using a rotary evaporator, and the residue is partitioned between 200 ml of ice water and 200 ml of ethyl acetate. The organic phase is discounted, whereas the aqueous phase is adjusted to pH=4 using hydrochloric acid and extracted twice with ethyl acetate. The organic extracts are dried using magnesium sulphate and concentrated under reduced pressure. The crude product is stored in the fridge and reacted further.

Example II

2-Cyclopropyl-3-dimethylaminoacrylonitrile

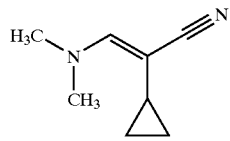

At 100° C., 25 g (292.8 mmol) of cyclopropylacetonitrile (obtainable by the process described in U.S. Pat. No. 3,454,575) and 25.5 g (30.2 ml, 146.4 mmol) of bis(dimethylamino)-tert-butyloxymethane are stirred under a riser pipe for 46 hours. Volatile components are evaporated under reduced pressure and the residue is subsequently distilled at 0.1 Torr and 60–65° C.

Yield 16.18 g (81% of theory)

In a manner analogous to Examples I and II, it is possible to prepare the corresponding cyclobutyl, cyclopentyl, cyclohexyl and 1-cyclopentene-1-yl derivatives.

Example III

Ethyl 5-amino-1-(2-fluorobenzyl)-1H-pyrazolo-3-carboxylate

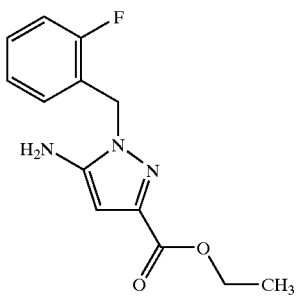

Under argon, 100 g (0.613 mol) of the sodium salt of ethyl cyanopyruvate (preparation analogously to Borsche and Manteuffel, Liebigs Ann. 1934, 512, 97) in 2.5 l of dioxane are mixed at room temperature and with efficient stirring with 111.75 g (75 ml, 0.98 mol) of trifluoroacetic acid, and the mixture is stirred for 10 min, during which a large fraction of the starting material dissolves. 85.93 g (0.613 mol) of 2-fluorobenzylhydrazine are then added, and the mixture is boiled overnight. After cooling, the precipitated sodium trifluoroacetate crystals are filtered off with suction and washed with dioxane, and the crude solution is reacted further.

Example IV

Ethyl 1-(2-fluorobenzyl)-1H-pyrazolo[3,4-b]pyridine-3-carboxylate

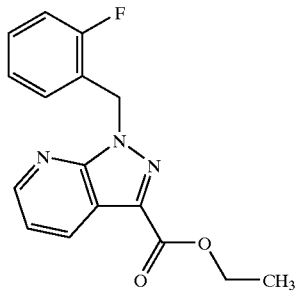

The solution obtained in Example III is mixed with 61.25 ml (60.77 g, 0.613 mol) of dimethylaminoacroleine and 56.28 ml (83.88 g, 0.736 mol) of trifluoroacetic acid and boiled under argon for 3 days. The solvent is subsequently evaporated under reduced pressure and the residue is added to 2 l of water and extracted three times with 1 l of ethyl acetate each time. The combined organic phases are dried with magnesium sulphate and concentrated using a rotary evaporator. The residue is chromatographed over 2.5 kg of silica gel, eluting with a toluene/toluene-ethyl acetate=4:1 gradient.

Yield: 91.6 g (49.9% of theory over two steps).

M.p. 85° C.

$R_f(SiO_2, T1E1)$: 0.83

Example V 1-(2-Fluorobenzyl)-1H-pyrazolo[3,4-b]pyridine-3-carboxamide

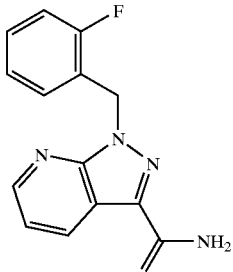

10.18 g (34 mmol) of the ester obtained in Example IV are initially charged in 150 ml of methanol which has been saturated with ammonia at 0–10° C. The mixture is stirred at room temperature for two days and subsequently concentrated under reduced pressure.

$R_f(SiO_2, T1E1)$: 0.33

Example VI

3-Cyano-1-(2-fluorobenzyl)-1H-pyrazolo[3,4-b]pyridine

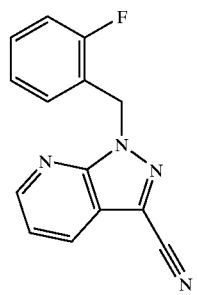

36.1 g (133 mmol) of 1-(2-fluorobenzyl)-1H-pyrazolo[3,4-b]pyridine-3carboxamide from Example V are dissolved in 330 ml of THF and mixed with 27 g (341 mmol) of pyridine. Over a period of 10 min, 47.76 ml (71.66 g, 341 mmol) of trifluoroacetic anhydride are subsequently added, during which the temperature rises to up to 40° C.

The mixture is stirred at room temperature overnight. The mixture is subsequently poured into 1 l of water and extracted three times with 0.5 l of ethyl acetate each time. The organic phase is washed with saturated sodium bicarbonate solution and with 1 N HCl, dried with MgSO$_4$ and concentrated using a rotary evaporator.

Yield: 33.7 g (100% of theory)

M.p.: 81° C.

R$_f$(SiO$_2$, T1E1): 0.74

Example VII

Methyl 1-(2-fluorobenzyl)-1H-pyrazolo[3,4-b]pyridine-3-carbox-imidate

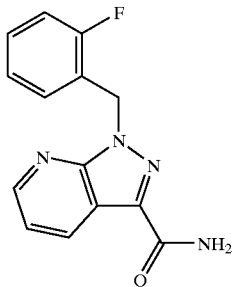

30.37 g (562 mmol) of sodium methoxide are dissolved in 1.5 l of methanol, and 36.45 g (144.5 mmol) of 3-cyano-1-(2-fluorobenzyl)-1H-pyrazolo[3,4-b]pyridine (from Example VII) are added. The mixture is stirred at room temperature for 2 hours and the resulting solution is used directly for the next step.

Example VIII 1-(2-Fluorobenzyl)-1H-pyrazolo[3,4-b]pyridine-3-carboxamidine

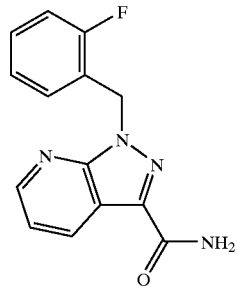

The solution of methyl (2-fluorobenzyl)-1H-pyrazolo[3,4-b]pyridine-3-carboximidate in methanol obtained from Example VII is admixed with 33.76 g (32.19 ml, 562 mmol) of glacial acetic acid and 9.28 g (173 mmol) of ammonium chloride and stirred under reflux overnight. The solvent is evaporated under reduced pressure, the residue is triturated thoroughly with acetone and the precipitated solid is filtered off with suction. The solid is added to 2 l of water, admixed with stirring with 31.8 g of sodium carbonate and extracted three times with a total of 1 l of ethyl acetate, and the organic phase is dried with magnesium sulphate and concentrated under reduced pressure.

Yield: 27.5 g (76.4% of theory over two steps)

M.p.: 86° C.

R$_f$(SiO$_2$, T1EtOH1): 0.08

Example IX 1-(2-Fluorobenzyl)-3-cyanoindazole

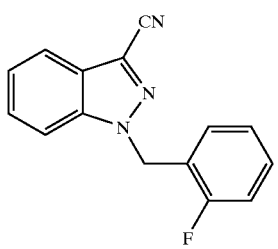

Under argon, 12.0 g (83.9 mmol) of 3-cyanoindazole [for the preparation, cf. Salkowski, Chem. Ber. 17 (1984), 508] were dissolved in 100 ml of abs. THF, and 20.6 g (109 mmol) of 2-fluorobenzyl bromide were added. With ice-cooling, 2.55 g (100 mmol) of sodium hydride (95 per cent) were added a little at a time. The mixture was stirred overnight at room temperature and then concentrated to about one quarter of its volume using a rotary evaporator and admixed with H$_2$O and ethyl acetate. The aqueous phase was re-extracted with ethyl acetate. The combined organic phases were dried over MgSO$_4$ and the solvent was distilled off using a rotary evaporator, leaving the product.

Yield: 19.5g (93%)

R$_f$ value: 0.69 (silica gel; cyclohexane/ethyl acetate 1:1)

Example X

1-(2-Fluorobenzyl)indazole-3-amidinium chloride

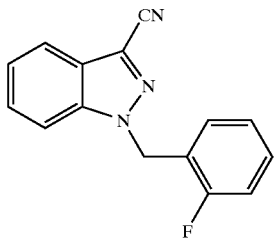

A sodium methoxide solution, which had been prepared from 190 mg (8.26 mmol) of NaOMe and 30 ml of abs. methanol, was added to a solution of 20.0 g (97.7 mmol) of 1-(2-fluorobenzyl)-3-cyanoindazole (from Example IX) in 200 ml of methanol, and the mixture was stirred at 40° C. for 22 h. After addition of 0.46 ml of acetic acid and 4.30 g of NH$_4$Cl, the mixture was stirred at 40° C. for another 24 h and subsequently concentrated to dryness using a rotary evaporator. The residue was taken up in acetone and the remaining precipitate was filtered off with suction, giving, after drying under high vacuum, the product in the form of a light-beige powder.

Yield: 20.5 g (84%)

M.p.: >230° C.

MS-EI: m/z(%)=268 (31, M$^+$ of the free base), 251 (15), 109 (100).

Example XI

2-Cyanocyclopropylacetamide

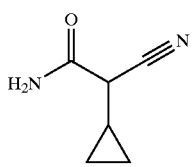

1.5 g (9.8 mmol) of ethyl 2-cyanocyclopropylacetate (preparation according to Li, J. Med. Chem. 1996, 39, 3070) are dissolved in 14 ml of methanolic ammonia (7N). After four days, the solution is concentrated using a rotary evaporator and the solid is washed with a little methanol.

Yield: 456 mg (37.5% of theory).

MS (DCI-NH$_3$): 142 (100%, M$^+$NH$_4$)

Example XII

2-Cyclopropylmalononitrile

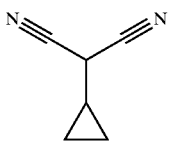

440 mg (3.54 mmol) of 2-cyanocyclopropylacetamide (from Example XI) are admixed twice with toluene which is then evaporated using a rotary evaporator to remove the methanol, and the substance is dissolved in 15 ml of tetrahydrofuran:dichloromethane (2:1). A total of 2.53 g (10.63 mmol) of Burgess reagent is added in three identical portions at intervals of 30 minutes. After a further 30 minutes, the reaction mixture is chromatographed directly over 20 g of silica gel using cyclohexane/ethyl acetate (2:1 to 1:1).

Yield: 122 mg (32.4% of theory)

R$_f$(SiO$_2$, C1E1): 0.65

Example XIII

1-Cyanomethyl-1-fluoromethyl-cyclopropane

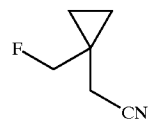

At 140° C., 8.85 g (72.2 mmol) of 1-chloromethyl-1-fluoromethyl-cyclopropane, 4.60 g (93.8 mmol) of sodium cyanide and 433 mg (2.89 mmol) of sodium iodide were heated in 72 ml of triethylene glycol at 140° C. for 30 minutes. The mixture was allowed to cool to room temperature and admixed with 150 ml each of dichloromethane and water, and the organic phase was washed with saturated sodium chloride solution, dried over MgSO$_4$ and concentrated to dryness at room temperature using a rotary evaporator. The liquid product was reacted further without any further purification.

Yield: 5.44 g (67%)

Example XIV

2-[(1-Fluoromethyl)cycloprop-1-yl]-2-formylacetonitrole

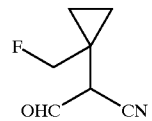

Under argon, 9.20 g (82.1 mmol) of potassium tert-butoxide were initially charged in 80 ml of anhydrous tetrahydrofuran (THF) and the mixture was mixed with a solution of 4.21 g (37.3 mmol) of 1-cyanomethyl-1-fluoromethyl-cyclopropane (Ex. XIII) and 9.24 g (125 mmol) of ethyl formiate in 20 ml of anhydrous THF. The mixture was stirred at room temperature for 3 hours and then concentrated to dryness using a rotary evaporator, and the residue was admixed with 150 ml each of ice water and ethyl acetate. The aqueous phase was separated off and adjusted to pH 4 using dilute hydrochloric acid. It was possible to isolate the product by extracting twice with 100 ml of ethyl acetate each time, drying of the organic phase over MgSO$_4$ and stripping off the solvent using a rotary evaporator. The product was used without any further purification for the next reaction.

Yield: 4.03 g (77%)

Preparation Examples

Example 1

3-(4-Amino-5-cyclopropylpyrimidin-2-yl)- 1-(2-fluorobenzyl)-1H-pyrazolo[3,4-b]pyridine

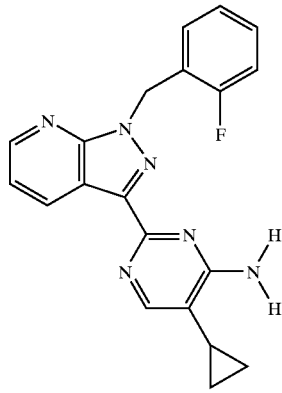

Procedure A 2 g (7.4 mmol) of the amidine from Example VIII are ground until it has a powder-like consistency. The lump-free starting material is mixed with 4 g (29.4 mmol) of 2-cyclopropyl-3-dimethylaminoacrylonitrile from Example II and mixed intimately, using spatular and ultrasonic bath, until a homogeneous milk has formed. Water pump vacuum is applied, causing the mixture to foam. With shaking, the mixture is subsequently immersed into an oil bath at 106° C., and the mixture becomes clear. After 2 hours, the content of the small flask begins to solidify. The mixture is left under reduced pressure at 106° C. overnight. The resulting solid is stirred with toluene, filtered off with suction and washed with ether. The residue is taken up in 50 ml of boiling acetonitrile and filtered off with suction. The residue obtained is taken up in 25 ml of boiling dimethylformamide and once more filtered off with suction. Both filtrates are combined and concentrated using a rotary evaporator.

Yield: 0.85 g (31.2% of theory)
M.p.: 210° C.
MS (ESI-POS): 361 (100%, M+H)
$^1$H-NMR (300 MHz, d$^6$-DMSO): 0.61 (m, 2H, 2-cyclopropyl), 0.9 (m, 2H, 2-cyclopropyl), 1.65 (m, 1H, 1-cyclopropyl), 5.7 (s, 2H, benzyl-CH$_2$), 6.98 (broad s, 2H, NH$_2$), 7.1–7.3 (peak cluster, 3H, aromatic benzylic H3,5,6), 7.3–7.4 (peak cluster, 2H, H5, benzylic H4), 8.0 (1H, pyrimidinyl-H6), 8.6 (d, 1H, H6), 8.95 (d, 1H, H4)

Procedure B 20.0 g (74.3 mmol) of the amidine from Example VIII and 28.4 g (260.0 mmol) of the crude 2-cyclopropyl-3-oxopropionitrile from Example I are added together in 280 ml of toluene and mixed in an ultrasonic bath, and the mixture is heated at reflux overnight. The solution is concentrated to half its volume using a rotary evaporator, cooled and filtered off with suction, and the filter residue is washed with ethyl acetate. The filtrate is concentrated and chromatographed over silica gel 60 (particle size 0.040–0.063 mm) using cyclohexane/ethyl acetate 1:1 as mobile phase. The residue is taken up in 50 ml of boiling toluene and filtered off with suction. Both solutions are combined, concentrated using a rotary evaporator and recrystallized from toluene.

Yield: 8.38 g (31.3% of theory).
R$_f$(SiO$_2$, C1E2): 0.23
M.p.: 209° C.

Procedure C (Method without Solvent)

103.7 mg (0.38 mmol) of the amidine from Example VIII and 168.1 mg (1.54 mmol) of the crude 2-cyclopropyl-3-oxopropionitrile from Example I are added together in 0.5 ml of toluene and mixed in an ultrasonic bath. The toluene is evaporated under reduced pressure and the mixture is heated to 100–105° C. without solvent in an open vessel. After one hour, the mixture is cooled, the residue is dissolved in dichloromethane and admixed with 1 g of silica gel and the mixture is concentrated using a rotary evaporator.

For purification, the substance is chromatographed over silica gel 60 (particle size 0.040–0.063 mm) using cyclohexane/ethyl acetate 1:1 as mobile phase.

Yield: 50.0 mg (36.0% of theory).
R$_f$(SiO$_2$, C1E2): 0.23

The following compounds (Ex. 2 to 5) are prepared analogously to the procedures mentioned above:

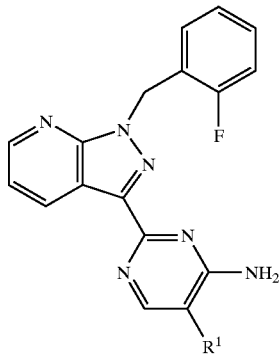

Example 2

3-(4-Amino-5-cyclobutylpyrimidin-2-yl)-1-(2-fluorobenzyl)-1H-pyrazolo[3,4-b]pyridine
R$^1$=cyclobutyl
M.p. 214° C.

Example 3

3-(4-Amino-5-cyclopentylpyrimidin-2-yl)-1-(2-fluorobenzyl)-1H-pyrazolo[3,4-b]pyridine
R$^1$=cyclopentyl
M.p. 208° C.

Example 4

3(4-Amino-5-cyclohexylpyrimidin-2-yl)-1-(2-fluorobenzyl)-1H-pyrazolo[3,4-b]pyridine
R$^1$=cyclohexyl
M.p. 213° C.

Example 5

3-(4-Amino-5-(1-cyclopenten-1-yl)-pyrimidin-2-yl)-1-(2-fluorobenzyl)-1H-pyrazolo[3,4-b]pyridine

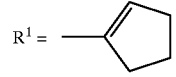

M.p. 228° C.

Example 6

3-(4-Amino-5-cyclopropylpyrimidin-2-yl)-1-(2-fluorobenzyl)-1H-pyrazolo[3,4-b]pyridine, hydrochloride 0.3 g (0.83 mmol) of 3-(4-amino-5-cyclopropylpyrimidin-2-yl)-1-(2-fluorobenzyl)-1H-pyrazolo[3,4-b]pyridine from Example 1 is dissolved in 50 ml of hot acetonitrile, and 0.9 ml of 1 N HCl (0.9 mmol) is added. The precipitated crystals are subsequently filtered off with suction.

Yield: 0.24 g (72.7% of theory)
M.p. 279° C.

Example 7

3-(4-Amino-5-cyclopropylpyrimidin-2-yl)-1-(2-fluorobenzyl)-1H-pyrazolo[3,4-b]pyridine, tosylate 0.3 g of 3-(4-amino-5-cyclopropylpyrimidin-2-yl)-1-(2-fluorobenzyl)-1H-pyrazolo[3,4-b]pyridine from Example 1 is dissolved in 50 ml of hot acetonitrile, and 160 mg of p-toluenesulphonic acid are added. After cooling to room temperature, the precipitated crystals are filtered off with suction.

Yield: 303 mg (68.8% of theory),
M.p. 203° C.

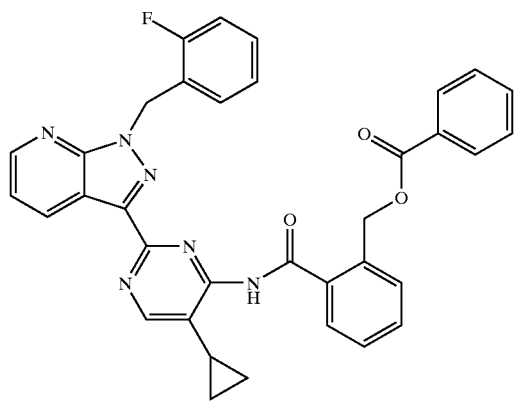

At room temperature, 105 mg (2.62 mmol) of sodium hydride (60% suspension in oil) are suspended in 20 ml of THF. 472 mg (1.31 mmol) of the amine from Example 1 in 10 ml of THF and 432 mg (1.57 mmol) of 2-(benzoyloxymethyl)benzoyl chloride in 5 ml of THF are added. The solution is admixed with water, extracted with ethyl acetate and washed with 1M hydrochloric acid and NaHCO₃ solution, dried with magnesium sulphate and concentrated under reduced pressure. The substance is digested repeatedly with cyclohexane.

Yield: 474 mg (60.4% of theory)
Rf: 0.61 (SiO₂, C1E2)
M.p.: 134–136° C.

Example 9

3-(5-Cyclopropyl-4-(2,2-dimethylpropanoyl)aminopyrimidin-2-yl)-1-(2-fluorobenzyl)-1H-pyrazolo[3,4-b]pyridine

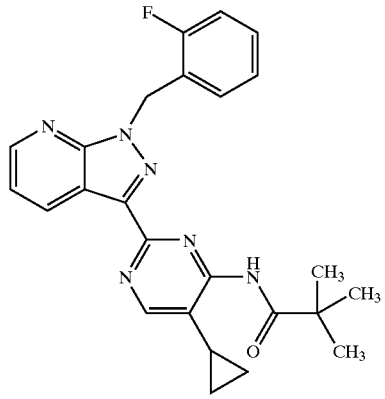

60 mg (0.17 mmol) of the amine from Example 1 are taken up in dichloromethane, 30 mg (0.25 mmol) of pivaloyl chloride, 26 mg (0.33 mmol) of pyridine and a catalytic amount of dimethylaminopyridine are added and the solution is stirred at room temperature for four hours. The solution is washed with 1N hydrochloric acid and saturated NaHCO₃ solution, dried with MgSO₄ and concentrated under reduced pressure. The crude product is chromatographed over silica gel using cyclohexane/ethyl acetate 1:1 as mobile phase.

Yield: 24.8 mg (33.5% of theory)
Rf: 0.59 (SiO₂, EA)

The following compounds can be obtained in an analogous manner:

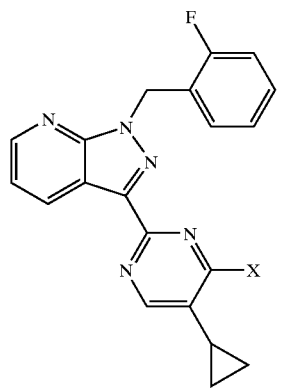

| Ex. | X | Yield (% of theory) | Rf (SiO₂) |
|---|---|---|---|
| 10 (from 1 and CH₃COCl) | 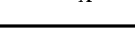 | 5.1 | 0.36 (C1E2) |

-continued

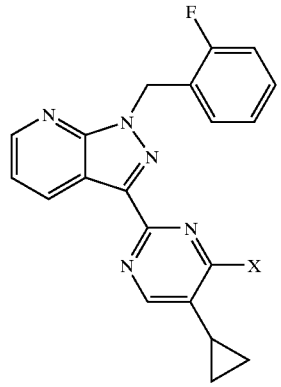

| Ex. | X | Yield (% of theory) | $R_f$ (SiO$_2$) |
|---|---|---|---|
| 11 (from 1 and CH$_3$COCl) | N(COCH$_3$)$_2$ with N-methyl (diacetyl methylamino) | 55.4 | 0.53 (C1E2) |
| 12 (from 1 and CH$_3$SO$_2$Cl) | NH-SO$_2$CH$_3$ (N-methylsulfonamide) | 11.8 | 0.79 (BABA) |
| 13 (from 1 and ethyl chloroformate) | N(CO$_2$Et)$_2$ with N-methyl | 42.9 | 0.64 (EA) |
| 14 (from 1 and the corresponding acyl chloride) | N-methyl amide of 3,3-dimethyl-3-(2,4,5-trimethyl-3,6-dioxocyclohexa-1,4-dienyl)propanamide | 17.0 | 0.29 (C1E1) |
| 15 (from 1 and 2-chloroethyl chloroformate) | 3-methyl-1,3-oxazolidin-2-one | 21.3 | 0.60 (EA) |

-continued

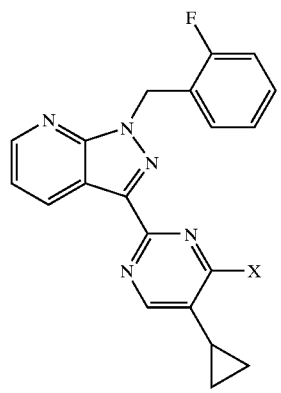

| Ex. | X | Yield (% of theory) | $R_f$ (SiO$_2$) |
|---|---|---|---|
| 16 (from 1 and o-azidobenzoyl chloride) | *N-methyl-2-azidobenzamide group* | 7.1 | 0.69 (EA) |
| 17 (from 1 and p-azidobenzoyl chloride) | *N-methyl-4-azidobenzamide group* | 72.9 | 0.37 (C1E1) |
| 18 (from 1 and m-azidobenzoyl chloride) | *N-methyl-3-azidobenzamide group* | 26.7 | 0.32 (C1E1) |

BABA: 50 ml of n-butylacetate+9 ml of n-butanol+25 ml of glacial acetic acid+15 ml of phosphate buffer pH 6 are shaken. The aqueous, lower phase that separates off is discarded.

Example 19

3-(5-Cyclopropyl-4-(ethoxymethylamino)pyrimidin-2-yl)-1-(2-fluorobenzyl)-1H-pyrazolo[3,4-b]pyridine

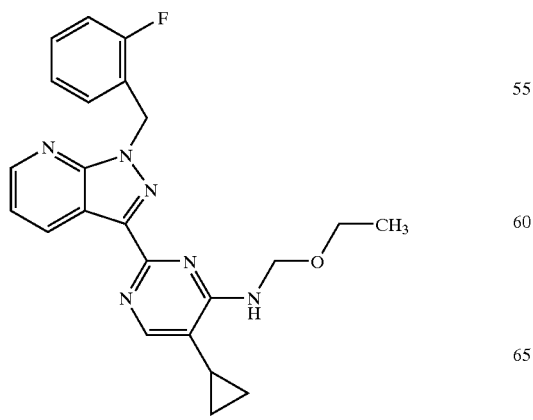

195.5 mg (0.54 mmol) of the amine from Example 1 are dissolved in 5 ml of ethanol. 0.9 ml (10.85 mmol) of a 37% strength solution of formaldehyde is added, the solution is heated at reflux for 24 hours. The solvents are evaporated under reduced pressure and the crude product is chromatographed over silica gel using cyclohexane/ethyl acetate 2:1 to ethyl acetate.

Yield: 87.1 mg (38.4% of theory)

Rf: 0.51 (SiO$_2$, EA)

The following compounds can be prepared analogously:

| Ex. | X | Yield (% of theory) | R$_f$ (SiO$_2$) |
|---|---|---|---|
| 20 (from 1 and formaldehyde) | | 70.9 | 0.38 (EA) |
| 21 (from 1 and acetaldehyde/ethanol) | | 28.0 | 0.59 (EA) |

Example 22

3-(5-Cyclopropyl-4-(propylaminocarbonylamino)pyrimidin-2-yl)-1-(2-fluorobenzyl)-1H-pyrazolo[3,4-b]pyridine

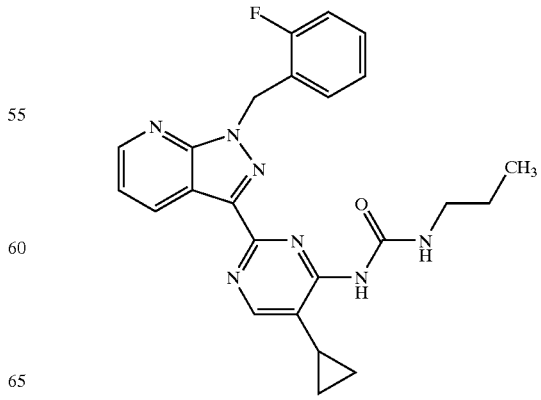

Under argon, 106 mg (0.29 mmol) of the amine from Example 1 are suspended in dichloromethane, and the mixture is admixed with 137.6 mg (1.62 mmol) of propyl isocyanate at 0° C. The mixture is heated at reflux for 38 hours. The substance is chromatographed over silica gel using cyclohexane/ethyl acetate 1:1 to ethyl acetate as mobile phase.

Yield: 52 mg (39.6% of theory)

Rf: 0.58 (SiO$_2$, EA)

The following compounds can be prepared analogously:

Under argon 1.08 g (6.00 mmol) of a solution of sodium methoxide (30 per cent in methanol) were admixed with 15 ml of abs. methanol and 1.83 g (6.00 mmol) of 1-(2-fluorobenzyl)indazol-3-amidinium chloride from Example X. The mixture was stirred at room temperature for 5 minutes, after which 816 mg (6.00 mmol) of 2-cyclopropyl-3-dimethylaminoacrylonitrile from Example II were added, and the mixture was heated under reflux overnight. After cooling to room temperature, the precipitate was filtered off with suction and stirred in pentane. Once more, the precipi-

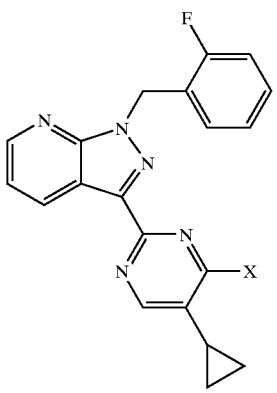

| Ex. | X | Yield (% of theory) | R$_f$ (SiO$_2$) |
|---|---|---|---|
| 23 (from 1 and m-chlorophenyl isocyanate) | | 55.8 | 0.60 (CE) |
| 24 (from 1 and hexyloxymethyl isocyanate) | | 11.3 | 0.29 (CE) |

Example 25

3-(4-Amino-5-cyclopropyl-2-pyrimidyl)-1-(2-fluorobenzyl)indazole

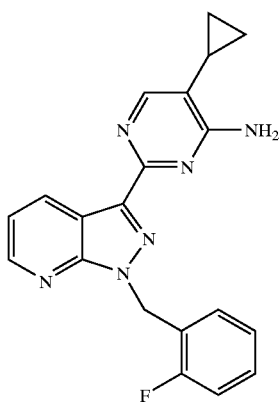

tate was filtered off with suction and dried under high vacuum, giving the product in the form of a virtually white solid.

Yield: 700 mg (32%)

M.p.: 218° C.

$^1$H-NMR: (400 MHz, D$_6$-DMSO), δ=0.61 (m, 2H, cyclo-Pr-CH$_2$), 0.91 (m, 2H, cyclo-Pr-CH$_2$), 1.67 (m, 1H, cyclo-Pr-CH), 5.80 (s, 2H, CH$_2$), 6.99 (brd. s, 2H, NH$_2$), 7.04–7.13 (m, 2H, Ar-H), 7.20–7.27 (m, 2H, Ar-H), 7.31–7.38 (m, 1H, Ar-H), 7.43 (t, 1H, Ar-H), 7.73 (d, 1H, Ar-H), 7.99 (s, 1H, Ar-H), 8.63 (d, 1H, Ar-H).

Example 26

3-(4,6-Diamino-5-cyclopropylpyrimidin-2-yl)-1-(2-fluorobenzyl)-1H-pyrazolo[3,4-b]pyridine

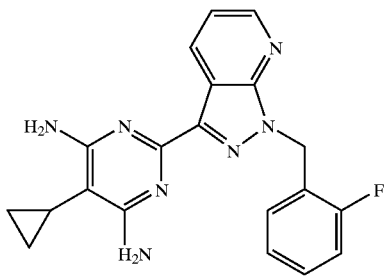

155 mg (0.57 mmol) of the amidine from Example VIII and 122 mg (1.15 mmol) of 2-cyclopropylmalonitrile from Ex. XII are added together in dichloromethane and heated in an open vessel to 105° C. After one hour, the reaction mixture solidifies. After three hours, the mixture is cooled, digested with toluene, filtered and dried under high vacuum.

Yield: 156 mg (72.3% of theory)

$R_f$(SiO$_2$, BABA): 0.37

M.p.: 198–200° C.

Analogously to Example 26, the following compounds are obtained:

| Ex. | X | Yield (% of theory) | $R_f$ (SiO$_2$) |
|---|---|---|---|
| 27 (from VIII and ![structure]) | ![structure] | 12.2 | 0.63 (BABA) |
| 28 (from VIII and ![structure]) | ![structure] | 13.2 | 0.70 (EA) |

-continued

| Ex. | X | Yield (% of theory) | $R_f$ (SiO$_2$) |
|---|---|---|---|
| 29 (from 28 by reaction with POCl$_3$/PhNMe$_2$) | [structure with Cl] | 100 | 0.75 (EA) |
| 30 (from 28 by reaction with PBr$_3$/PhNMe$_2$) | [structure with Br] | 21.9 | 0.19 (SiO$_2$, C1E1) |

Example 31

3-[4-Amino-5-(1-fluoromethyl)cycloprop-1-yl]-pyrimidin-2-yl)-1-(2-fluorobenzyl)-1H-pyrazolo[3,4-b]pyridine

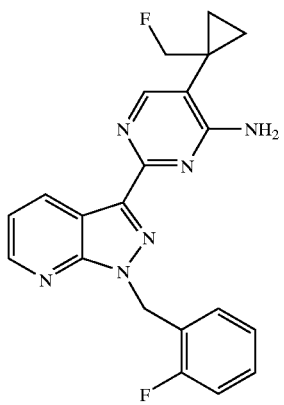

1.00 g (3.70 mmol) of the amidine from Ex. VIII and 1.83 g (13.0 mmol) of 2-[(1-fluoromethyl)cycloprop-1-yl]-2-formylacetonitrile from Ex. XIV were suspended in 30 ml of toluene. The mixture was sonicated with ultrasound for five minutes and subsequently heated under reflux. The mixture was concentrated using a rotary evaporator and then chromatographed over silica gel (C→C1:E1→EA). The most polar fraction had to be subjected to another column chromatography, again using the gradient (C/EA) but with addition of in each case 1% of triethylamine to the mobile phase.

Yield: 486 mg (34% of theory)

M.p.: 220° C.

$R_f$ value: 0.19(C1:E1)

What is claimed is:

1. A compound of the formula (I)

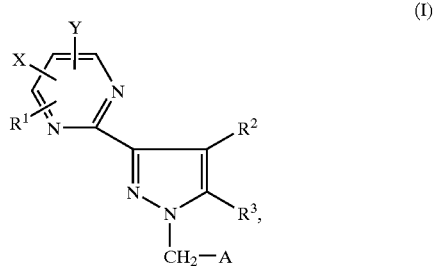

in which at least one of the substituents R$^1$, X and Y represents saturated or partially unsaturated C$_3$–C$_8$-cycloalkyl, which may optionally be mono- or polysubstituted by amino, azido, formyl, mercaptyl, carboxyl, hydroxyl, morpholino, piperidino, pyrrolidino, sulphonamino, straight-chain, cyclic or branched acyl, acylamino, alkoxy, benzyloxy, alkylamino, dialkylamino, alkylsulphonyl, alkylsulphonamino, alkylthio, alkoxycarbonyl having in each case up to 6 carbon atoms, nitro, cyano, halogen, phenyl and/or is optionally substituted by straight-chain or branched or cyclic alkyl having up to 6 carbon atoms which for its part may be substituted by amino, mercaptyl, carboxyl, hydroxyl, morpholino, piperidino, pyrrolidino, straight-chain, cyclic or branched acyl, acylamino, alkoxy, alkylamino, dialkylamino, alkylsulphonyl, alkylthio, phenyl, alkylsulphonamino, alkoxycarbonyl having in each case up to 6 carbon atoms, nitro, cyano, halogen, and where the optionally remaining radicals $R^1$, X and/or Y are identical or different and each represents hydrogen, azido, formyl, mercaptyl, carboxyl, hydroxyl, straight-chain or branched acyl, alkoxy, alkylthio or alkoxycarbonyl having in each case up to 6 carbon atoms, nitro, cyano, halogen, phenyl or straight-chain or branched alkenyl or alkinyl having in each case up to 6 carbon atoms or alkyl having up to 20 carbon atoms, where both alkenyl, alkinyl and/or alkyl may optionally be substituted by hydroxyl, amino, azido, carboxyl, straight-chain or branched acyl, alkoxy, alkoxycarbonyl or acylamino having in each case up to 5 carbon atoms, aryl having 6 to 10 carbon atoms, halogen, cyano, dialkylamino having up to 6 carbon atoms, alkylamino having up to 6 carbon atoms and/or cycloalkyl having 3 to 8 carbon atoms or by a radical of the formula —$OR^4$, in which
$R^4$ represents straight-chain or branched acyl having up to 5 carbon atoms, and/or the optionally remaining radicals $R^1$, X and/or Y each represents a radical of the formula

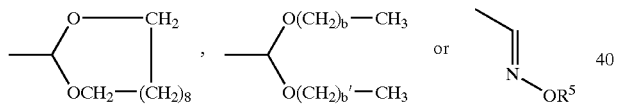

in which
a, b and b' are identical or different and represent a number 0, 1, 2 or 3,
$R^5$ represents hydrogen or straight-chain or branched alkyl having up to 4 carbon atoms, and/or the optionally remaining radicals $R^1$, X and/or Y each represent a 1,3-oxazolidin-2-on-3-yl group which is optionally mono- or polysubstituted by identical or different substituents from the group consisting of straight-chain or branched alkyl having up to 6 carbon atoms which is optionally substituted by hydroxyl, amino, halogen, carboxyl, straight-chain or branched acyl, alkoxy, alkoxycarbonyl or acylamino having in each case up to 5 carbon atoms, and/or the optionally remaining radicals $R^1$, X and/or Y each represent straight-chain or branched acyl having up to 6 carbon atoms which is optionally substituted by halogen, or represent straight-chain or branched acyloxy having up to 6 carbon atoms, or represent arylthio having 6 to 10 carbon atoms, and/or the optionally remaining radicals $R^1$, X and/or Y represent radicals of the formulae —$SO_3H$ or $S(O)_2R^6$, in which
c represents a number 1 or 2,
$R^6$ represents straight-chain or branched alkyl having 1 to 10 carbon atoms, cycloalkyl having 3 to 8 carbon atoms, or aryl having 6 to 10 carbon atoms where the ring systems may optionally be substituted by halogen or by straight-chain or branched alkyl or alkoxy having in each case up to 4 carbon atoms, and/or the optionally remaining radicals $R^1$, X and/or Y each represent a radical of the formula $PO(OR^7)(OR^8)$, in which
$R^7$ and $R^8$ are identical or different and each represents hydrogen, straight-chain or branched alkyl having up to 8 carbon atoms or cycloalkyl having 3 to 8 carbon atoms, aryl having 6 to 10 carbon atoms or benzyl, and/or the optionally remaining radicals $R^1$, X and/or Y each represent oxycycloalkyl having 3 to 8 carbon atoms or represent radicals of the formulae —NH—C(=NH)$NH_2$, CON=C($NH_2$)$_2$ or —C=NH($NH_2$), (CO)$_d$$NR^9R^{10}$ or —$NHCONR^{9'}R^{10'}$, in which
d represents a number 0 or 1,
$R^9$ and $R^{10}$ are identical or different and each represents hydrogen, straight-chain or branched alkyl having up to 14 carbon atoms or cycloalkyl having 3 to 14 carbon atoms, or aryl having 6 to 10 carbon atoms, where the abovementioned radicals may optionally be substituted by aryl having 6 to 10 carbon atoms, cycloalkyl having 3 to 7 carbon atoms, hydroxyl, amino or straight-chain or branched alkoxy, acyl or alkoxycarbonyl having in each case up to 6 carbon atoms, and in the case that d=0,
$R^9$ and $R^{10}$ may also represent straight-chain, branched or cyclic acyl having up to 14 carbon atoms, straight-chain or branched hydroxyalkyl having up to 6 carbon atoms, straight-chain or branched alkoxyalkyl having a total of up to 12 carbon atoms, straight-chain or branched alkoxycarbonyl or acyloxyalkyl having in each case up to 6 carbon atoms or a radical of the formula —$SO_2R^{11}$ or radicals of the formulae

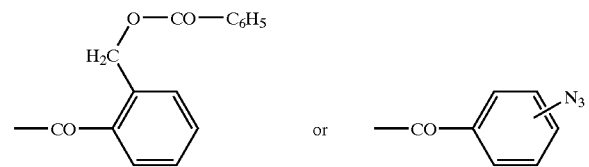

in which
$R^{11}$ represents straight-chain or branched alkyl having up to 4 carbon atoms, and/or
$R^9$ and $R^{10}$ represents radicals of the formulae

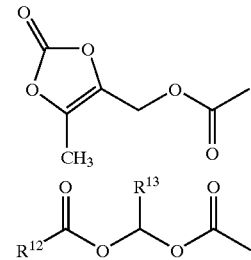

-continued

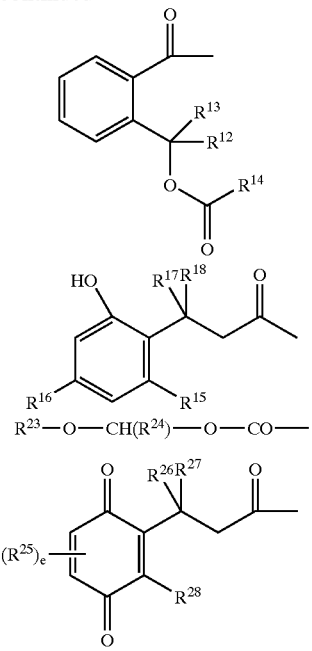

$R^{23}$—O—CH($R^{24}$)—O—CO— in which
$R^{12}$, $R^{13}$ and $R^{15}$ to $R^{18}$ and $R^{23}$ to $R^{28}$ are identical or different and each represents hydrogen or straight-chain or branched alkyl having up to 4 carbon atoms,
e represents a number 0, 1 or 2, and
$R^{14}$ represents straight-chain or branched alkyl having up to 6 carbon atoms or cycloalkyl having 3 to 8 carbon atoms,
$R^{9'}$ and $R^{10'}$ are identical or different and each represents hydrogen; alkyl having up to 14 carbon atoms which is optionally substituted by hydroxyl or alkoxy having up to 8 carbon atoms; aryl having 6 to 10 carbon atoms which is optionally substituted by halogen,
$R^2$ and $R^3$ form, together with the double bond, a fused phenyl ring or a fused 6-membered aromatic heterocycle having up to 2 N atoms as the heteroatom(s),
which is optionally substituted up to 3 times by identical or different substituents from the group consisting of formyl, carboxyl, hydroxyl, mercaptyl, straight-chain or branched acyl, alkylthio or alkoxycarbonyl having in each case up to 6 carbon atoms, nitro, cyano, halogen or straight-chain or branched alkyl or alkoxy having in each case up to 6 carbon atoms which for its part may be substituted by hydroxyl, amino, carboxyl, straight-chain or branched acyl, alkoxy or alkoxycarbonyl having in each case up to 5 carbon atoms,
and/or the fused phenyl ring or the fused 6-membered aromatic heterocycle is optionally substituted by a group of the formula —$NR^{29}R^{30}$,
in which
$R^{29}$ and $R^{30}$ are identical or different and each represents hydrogen or straight-chain or branched alkyl having up to 6 carbon atoms, or
$R^{29}$ represents hydrogen and
$R^{30}$ represents acyl having up to four carbon atoms
and/or the fused phenyl ring or fused 6-membered aromatic heterocycle are optionally substituted by phenyl which for its part may be substituted up to 2 times by identical or different substituents from the group consisting of halogen, straight-chain or branched alkyl and alkoxy having in each case up to 6 carbon atoms
and/or the fused phenyl ring or the fused 6-membered aromatic heterocycle are optionally substituted by a group of the formula —N=CH—$NR^{31}R^{32}$,
in which
$R^{31}$ and $R^{32}$ are identical or different and each represents hydrogen, phenyl or straight-chain or branched alkyl having up to 6 carbon atoms,
A represents phenyl or pyrimidyl group,
which is optionally substituted up to 3 times by identical or different substituents from the group consisting of amino, mercaptyl, hydroxyl, formyl, carboxyl, straight-chain or branched acyl, alkylthio, alkyloxyacyl, alkoxy or alkoxycarbonyl having in each case up to 6 carbon atoms, nitro, cyano, trifluoromethyl, azido, halogen, phenyl and straight-chain or branched alkyl having up to 6 carbon atoms which for its part may be substituted by hydroxyl, carboxyl, straight-chain or branched acyl, alkoxy or alkoxycarbonyl having in each case up to 5 carbon atoms, and/or
is substituted by a group of the formula —(CO)$_f$—$NR^{33}R^{34}$,
in which
f represents a number 0 or 1,
$R^{33}$ and $R^{34}$ are identical or different and represent hydrogen, phenyl, benzyl or straight-chain or branched alkyl or acyl having in each case up to 5 carbon atoms,
or a pharmaceutically acceptable isomeric form or salt thereof.

2. The compound according to claim 1,
in which
at least one of the substituents $R^1$, X and Y represents cyclopropyl, cyclobutyl, cyclopentenyl, cyclohexyl or cycloheptyl which may optionally be mono- or polysubstituted by amino, azido, formyl, mercaptyl, carboxyl, hydroxyl, morpholino, piperidino, pyrrolidino, sulphonamino, straight-chain, cyclic or branched acyl, acylamino, alkoxy, benzyloxy, alkylamino, dialkylamino, alkylsulphonyl, alkylsulphonamino, alkylthio, alkoxycarbonyl having in each case up to 4 carbon atoms, nitro, cyano, halogen, phenyl and/or is optionally substituted by
straight-chain or branched or cyclic alkyl having up to 4 carbon atoms which for its part may be substituted by amino, mercaptyl, carboxyl, hydroxyl, morpholino, piperidino, pyrrolidino, straight-chain, cyclic or branched acyl, acylamino, alkoxy, alkylamino, dialkylamino, alkylsulphonyl, alkylthio, phenyl, alkylsulphonamino, alkoxycarbonyl having in each case up to 4 carbon atoms, nitro, cyano, halogen,
and where the optionally remaining radicals $R^1$, X and/or Y are identical or different and each represents hydrogen, azido, formyl, mercaptyl, carboxyl, hydroxyl, straight-chain or branched acyl, alkoxy, alkylthio or alkoxycarbonyl having in each case up to 4 carbon atoms, nitro, cyano, halogen, phenyl or straight-chain or branched alkenyl or alkinyl having in each case up to 4 carbon atoms or alkyl having up to 18 carbon atoms, where both alkenyl, alkinyl and/or alkyl may optionally be substituted by hydroxyl, amino, azido, carboxyl, straight-chain or branched acyl, alkoxy, alkoxycarbonyl or acylamino having in each case up to 4 carbon atoms, phenyl, naphthyl or pyridyl, halogen, cyano, dialkylamino having up to 6 carbon atoms, alkylamino having up to 4 carbon atoms and/or cyclopropyl, cyclopentyl, cyclohexyl or by a radical of the formula —OR$^4$, in which
$R^4$ represents straight-chain or branched acyl having up to 4 carbon atoms, and/or the optionally remaining radicals $R^1$, X and/or Y each represent a radical of the formula

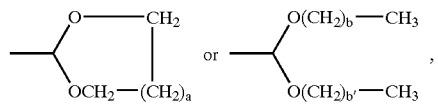

in which
a, b and b' are identical or different and represent a number 0, 1 or 2, and/or the optionally remaining radicals $R^1$, X and/or Y each represent a 1,3-oxazolidin-2-on-3-yl group which is optionally mono- or polysubstituted by identical or different substituents from the group consisting of straight-chain or branched alkyl having up to 4 carbon atoms which is optionally substituted by hydroxyl, amino, halogen, carboxyl, straight-chain or branched acyl, alkoxy, alkoxycarbonyl or acylamino having in each case up to 4 carbon atoms, and/or the optionally remaining radicals $R^1$, X and/or Y each represent straight-chain or branched acyl having up to 4 carbon atoms which is optionally substituted by halogen, or represent straight-chain or branched acyloxy having up to 4 carbon atoms, or represents phenylthio, and/or represent radicals of the formulae —SO$_3$H or S(O)$_c$R$^6$, in which
c represents a number 1 or 2,
$R^6$ represents straight-chain or branched alkyl having 1 to 8 carbon atoms, or phenyl, where the ring systems may optionally be substituted by halogen or by straight-chain or branched alkyl or alkoxy having in each case up to 3 carbon atoms, and/or the optionally remaining radicals $R^1$, X and/or Y each represent a radical of the formula PO(OR$^7$)(OR$^8$), in which
$R^7$ and $R^8$ are identical or different and each represents hydrogen, straight-chain or branched alkyl having up to 4 carbon atoms or cyclopropyl, cyclopentyl, phenyl or benzyl, and/or the optionally remaining radicals $R^1$, X and/or Y each represent oxycycloalkyl having 3 to 6 carbon atoms or represent radicals of the formulae —NH—C(=NH)NH$_2$, —CON=C(NH$_2$)$_2$ or —C=NH(NH$_2$), (CO)$_d$NR$^9$R$^{10}$ or —NHCONR$^9$'R$^{10}$', in which
d represents a number 0 or 1,
$R^9$ and $R^{10}$ are identical or different and each represents hydrogen, straight-chain or branched alkyl having up to 4 carbon atoms or cyclopropyl, cyclopentyl, cyclohexyl, or phenyl,
where the abovementioned radicals may optionally be substituted by phenyl, cyclopropyl, cyclopentyl, hydroxyl, amino or straight-chain or branched alkoxy, acyl or alkoxycarbonyl having in each case up to 4 carbon atoms, and in the case that d=0,
$R^9$ and $R^{10}$ may also represent straight-chain, branched or cyclic acyl having up to 6 carbon atoms, straight-chain or branched hydroxyalkyl having up to 4 carbon atoms, straight-chain or branched alkoxyalkyl having a total of up to 10 carbon atoms, straight-chain or branched alkoxycarbonyl or acyloxyalkyl having in each case up to 4 carbon atoms or a radical of the formula —SO$_2$R$^{11}$ or a radical of the formulae

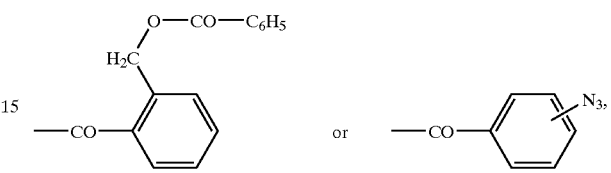

in which
$R^{11}$ represents straight-chain or branched alkyl having up to 3 carbon atoms, and/or
$R^9$ and $R^{10}$ represents radicals of the formulae

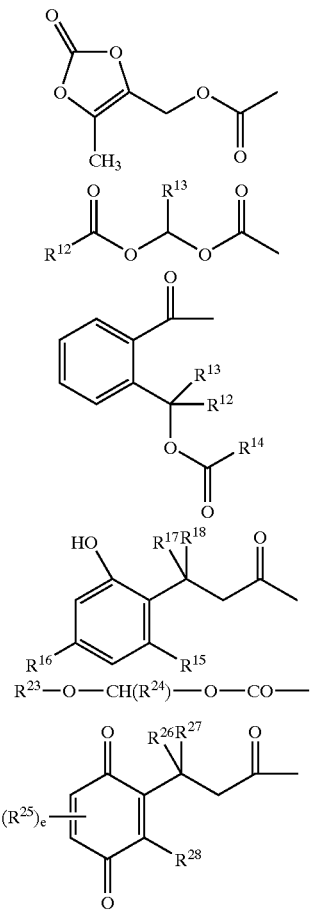

in which
$R^{12}$, $R^{13}$ and $R^{15}$ to $R^{18}$ and $R^{23}$ to $R^{28}$ are identical or different and each represents hydrogen or straight-chain or branched alkyl having up to 4 carbon atoms,
e represents a number 0, 1 or 2, and
$R^{14}$ represents straight-chain or branched alkyl having up to 6 carbon atoms or cycloalkyl having 3 to 8 carbon atoms, $R^{9'}$ and $R^{10'}$ are identical or different and each represents hydrogen; alkyl having up to 4 carbon atoms which is optionally substituted by hydroxyl or alkoxy having up to 7 carbon atoms, phenyl which is optionally substituted by halogen, $R^2$ and $R^3$, together with the double bond, form a fused phenyl, pyridyl, pyrimidinyl, pyrazinyl or pyridazinyl ring, which are optionally substituted up to 2 times by identical or different substituents from the group consisting of formyl, carboxyl, hydroxyl, mercaptyl, straight-chain or branched acyl, alkylthio or alkoxycarbonyl having in each case up to 5 carbon atoms, nitro, cyano, azido, fluorine, chlorine, bromine or straight-chain or branched alkyl or alkoxy having in each case up to 5 carbon atoms which for its part may be substituted by hydroxyl, amino, carboxyl, straight-chain or branched acyl, alkoxy or alkoxycarbonyl having in each case up to 4 carbon atoms, and/or the abovementioned heterocyclic rings or phenyl are optionally substituted by a group of the formula $-NR^{29}R^{30}$, in which $R^{29}$ and $R^{30}$ are identical or different and represent hydrogen or straight-chain or branched alkyl having up to 4 carbon atoms or $R^{29}$ represents hydrogen and $R^{30}$ represents formyl and/or the abovementioned fused phenyl, pyridyl, pyrimidinyl, pyrazinyl or pyridazinyl rings are optionally substituted by phenyl which for its part may be substituted by fluorine, chlorine, bromine or by straight-chain or branched alkyl or alkoxy having in each case up to 4 carbon atoms, A represents phenyl or pyrimidyl group which is optionally substituted up to 2 times by identical or different substituents from the group consisting of hydroxyl, formyl, carboxyl, straight-chain or branched acyl, alkylthio, alkyloxyacyl, alkoxy or alkoxycarbonyl having in each case up to 4 carbon atoms, fluorine, chlorine or bromine, or a pharmaceutically acceptable isomeric form or salt thereof.

3. The compound according to claim 1, in which at least one of the substituents $R^1$, X and Y represents cyclopropyl which is optionally substituted by hydroxyl or fluoromethyl, or represents cyclobutyl, cyclopentenyl, cyclopentyl or cyclohexyl, and where the optionally remaining radicals $R^1$, X and/or Y are identical or different and each represents hydrogen, hydroxyl, halogen or azido, and/or represent a 1,3-oxazolidin-2-on-3-yl group which is optionally mono- or polysubstituted by identical or different substituents from the group consisting of straight-chain or branched alkyl having up to 4 carbon atoms which is optionally substituted by hydroxyl, amino, halogen, carboxyl, straight-chain or branched acyl, alkoxy, alkoxycarbonyl or acylamino having in each case up to 4 carbon atoms, and/or represent straight-chain or branched acyl having up to 4 carbon atoms which is optionally substituted by halogen, or represent straight-chain or branched acyloxy having up to 4 carbon atoms, and/or represent radicals of the formulae $-SO_3H$ or $S(O)_cR^6$, in which c represents a number 1 or 2, $R^6$ represents straight-chain or branched alkyl having 1 to 8 carbon atoms, or phenyl, where the ring systems may optionally be substituted by halogen or by straight-chain or branched alkyl or alkoxy having in each case up to 3 carbon atoms, and/or represent a radical of the formula $PO(OR^7)(OR^8)$, in which $R^7$ and $R^8$ are identical or different and each represents hydrogen, straight-chain or branched alkyl having up to 4 carbon atoms or cyclopropyl, cyclopentyl, phenyl or benzyl, and/or represent oxycycloalkyl having 3 to 6 carbon atoms or represent radicals of the formulae $-CON=C(NH_2)_2$ or $-C=NH(NH_2)$ or $(CO)_dNR^9R^{10}$ or $NHCONR^{12'}R^{13'}$, in which d represents a number 0 or 1, $R^9$ and $R^{10}$ are identical or different and each represents hydrogen, straight-chain or branched alkyl having up to 4 carbon atoms or cyclopropyl, cyclopentyl, cyclohexyl or phenyl, and in the case where d=0

$R^9$ and $R^{10}$ also represent straight-chain, branched or cyclic acyl having up to 5 carbon atoms, straight-chain or branched hydroxyalkyl having up to 3 carbon atoms, straight-chain or branched alkoxyalkyl having a total of up to 8 carbon atoms, straight-chain or branched alkoxy carbonyl or acyloxyalkyl having in each case up to 3 carbon atoms or a radical of the formula $-SO_2R^{11}$ or a radical of the formulae

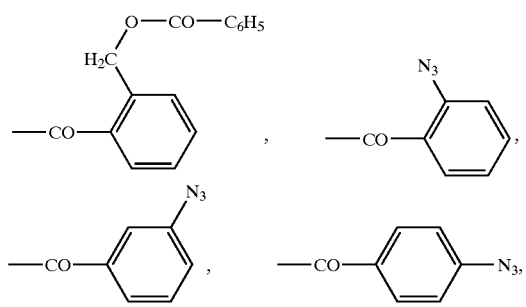

in which $R^{11}$ represents straight-chain or branched alkyl having up to 4 carbon atoms and/or $R^9$ and $R^{10}$ represents radicals of the formulae

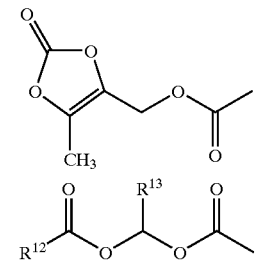

-continued

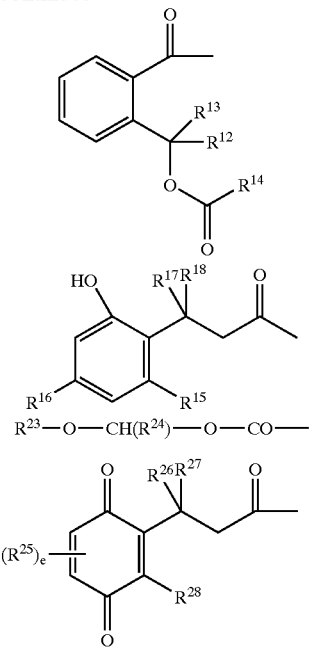

R²³—O—CH(R²⁴)—O—CO— in which
R¹², R¹³ and R¹⁵ to R¹⁸ and R²³ to R²⁸ are identical or different and represent hydrogen or straight-chain or branched alkyl having up to 4 carbon atoms,
e represents a number 0, 1 or 2 and
R¹⁴ represents straight-chain or branched alkyl having up to 6 carbon atoms or cycloalkyl having 3 to 8 carbon atoms,
R⁹' and R¹⁰' are identical or different and represent hydrogen; alkyl having up to 4 carbon atoms which is optionally substituted by hydroxyl or alkoxy having up to 7 carbon atoms, phenyl which is optionally substituted by halogen,
R² and R³ form, together with the double bond, a phenyl, pyridyl or pyrimidinyl ring,
A represents phenyl or pyrimidyl group, each of which is optionally substituted by fluorine, chlorine or bromine,
or a pharmaceutically acceptable isomeric form or salt thereof.

4. The compound according to claim 1,
in which
R¹, X and Y are attached to the pyrimidine ring as follows

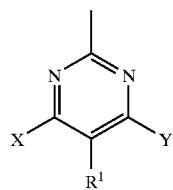

and
R¹ represents an optionally substituted cyclopropyl, cyclobutyl, cyclopentenyl, cyclopentyl, cyclohexyl, 1-hydroxycyclopropyl or 1-(fluoromethyl)cyclopropyl radical,
X represents NH₂ and
Y represents hydrogen or NH₂.

5. The compound according to claim 4, in which R¹ represents an optionally substituted cyclopropyl radical.

6. A process for preparing the compounds of the general formula (I) according to claim 1,
characterized in that
depending on the various meanings of the heterocycles listed above are under R² and R³, compounds of the general formula (II)

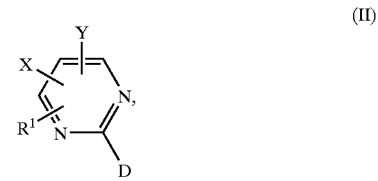

(II)

in which
R¹, X and Y are each as defined above in claim 1, and
D represents radicals of the formulae

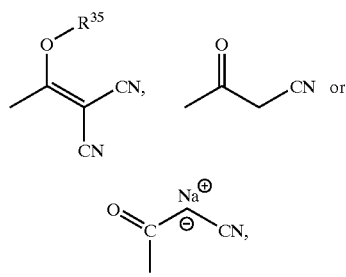

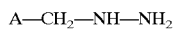

in which
R³⁵ represents C₁–C₄-alkyl
are converted, by reaction with compounds of the general formula (III)

A—CH₂—NH—NH₂ (III), in which
A is as defined above in claim 1,
in inert solvents into the compounds of the general formula (IV) or (IVa)

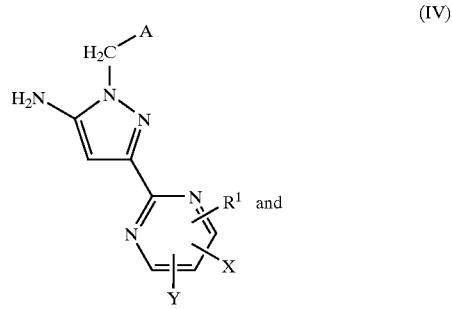

(IV)

-continued

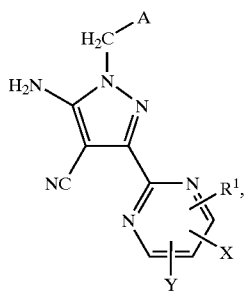

(IVa)

in which

A, X, Y and R¹ are each as defined above in claim 1, and, in the case of the compounds of the general formula (IVa), are subsequently cyclized with carboxylic acids, nitriles, formamides or guanidium salts, and in the case of the compounds of the general formula (IV), are cyclized with 1,3-dicarbonyl derivatives, their salts, tautomers, enol ethers or enamines in the presence of acids.

7. The process of claim 6, wherein said compound of general formula (IV) further is cyclized with 1,3-dicarbonyl derivatives, their salts, tautomers, enol ethers or enamines in the presence of acids under microwave irradiation.

8. A pharmaceutical composition comprising at least one compound of the formula (I) according to claim 1 and a pharmaceutically acceptable carrier.

9. A pharmaceutical composition comprising at least one compound of the formula (I) according to claim 1 in combination with at least one organic nitrate or NO donor.

10. A pharmaceutical composition comprising at least one compound of the formula (I) according to claim 1 in combination with at least one compound which inhibits the degradation of cyclic guanosine monophosphate (cGMP).

11. A method of treating the cardiovascular disease hypertension, comprising administering to a hypertensive mammal an effective amount of a compound according to claim 1.

12. The method of claim 11, wherein said compound of the formula (I) according to claim 1 is administered in combination with an organic nitrate or NO donor.

13. The method of claim 11, wherein said compound of the formula (I) according to claim 1 is administered in combination with a compound that inhibits the degradation of cyclic guanosine monophosphate (cGMP).

\* \* \* \* \*